(12) United States Patent
Esfandiari

(10) Patent No.: US 7,879,597 B2
(45) Date of Patent: *Feb. 1, 2011

(54) DUAL PATH IMMUNOASSAY DEVICE

(75) Inventor: Javanbakhsh Esfandiari, Stony Brook, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 362 days.

This patent is subject to a terminal disclaimer.

(21) Appl. No.: 11/908,071

(22) PCT Filed: Mar. 10, 2006

(86) PCT No.: PCT/US2006/008688

§ 371 (c)(1),
(2), (4) Date: Sep. 7, 2007

(87) PCT Pub. No.: WO2006/099191

PCT Pub. Date: Sep. 21, 2006

(65) Prior Publication Data

US 2008/0318341 A1     Dec. 25, 2008

Related U.S. Application Data

(63) Continuation-in-part of application No. 11/172,298, filed as application No. PCT/US06/08688 on Mar. 10, 2006, now Pat. No. 7,189,522.

(60) Provisional application No. 60/660,695, filed on Mar. 11, 2005, provisional application No. 60/680,884, filed on May 13, 2005, provisional application No. 60/741,628, filed on Dec. 2, 2005.

(51) Int. Cl.
    *G01N 33/53*    (2006.01)

(52) U.S. Cl. .................. 435/287.2; 435/7.1; 435/287.1; 435/287.7; 435/287.8; 435/287.9; 435/288.3; 435/288.7; 435/805; 436/501; 436/514; 436/518; 436/807; 436/810

(58) Field of Classification Search .................. 435/7.1, 435/287.1, 287.7, 287.8, 287.9, 288.3, 288.7, 435/805; 436/501, 514, 518, 807, 810
See application file for complete search history.

(56) References Cited

U.S. PATENT DOCUMENTS

| 3,960,488 A | 6/1976 | Giaever |
| 4,041,146 A | 8/1977 | Giaever |
| 4,042,335 A | 8/1977 | Clement |

(Continued)

*Primary Examiner*—Bao-Thuy L Nguyen
(74) *Attorney, Agent, or Firm*—Gordon & Jacobson, PC

(57) ABSTRACT

The systems of the invention include test cells with a first sorbent material defining a first flow path for a solution, a second sorbent material defining a second flow path distinct from the first flow path for a sample, and a test site with immobilized antigens or antibodies or other ligand binding molecules such as aptamers, nucleic acids, etc. located at the junction of the first and second sorbent materials for identifying one or more ligands. The first and second sorbent strips touch each other at the test site location. The test cell may be used to test for pregnancy, HIV (including different HIV antigens or peptides), tuberculosis, prion, urin-analysis/drug, cardiac markers, cancer markers, Chagas, Chlamydia, dental bacteria (SM/LC), influenza A, influenza B, adenovirus, rotavirus, strep A, other bacteria or viruses, etc., and veterinary applications such as CPV, FIV, FeLV, heartworm, etc., although it is not limited to those applications.

9 Claims, 22 Drawing Sheets

U.S. PATENT DOCUMENTS

| | | |
|---|---|---|
| 4,059,405 A | 11/1977 | Sodickson et al. |
| 4,094,647 A | 6/1978 | Deutsch et al. |
| 4,144,306 A | 3/1979 | Figueras |
| 4,235,601 A | 11/1980 | Deutsch et al. |
| 4,323,536 A | 4/1982 | Columbus |
| 4,361,537 A | 11/1982 | Deutsch et al. |
| 4,522,786 A | 6/1985 | Ebersole |
| 4,532,107 A | 7/1985 | Siddigi |
| 4,588,555 A | 5/1986 | Provonchee |
| 4,595,654 A | 6/1986 | Reckel et al. |
| 4,632,901 A | 12/1986 | Valkirs et al. |
| 4,668,619 A | 5/1987 | Greenquist et al. |
| 4,740,468 A | 4/1988 | Weng et al. |
| 4,786,595 A | 11/1988 | Arai et al. |
| 4,826,759 A | 5/1989 | Guire et al. |
| 4,855,240 A | 8/1989 | Rosenstein et al. |
| 4,857,453 A | 8/1989 | Ullman et al. |
| 4,870,003 A | 9/1989 | Kortright et al. |
| 4,886,742 A | 12/1989 | Kortright et al. |
| 4,906,439 A | 3/1990 | Grenner |
| 4,912,034 A | 3/1990 | Kalra et al. |
| 4,920,046 A | 4/1990 | McFarland et al. |
| 4,943,522 A | 7/1990 | Eisinger et al. |
| 4,956,275 A | 9/1990 | Zuk et al. |
| 4,956,302 A | 9/1990 | Gordon et al. |
| 4,960,691 A | 10/1990 | Gordon et al. |
| 4,960,710 A | 10/1990 | Lau |
| 4,981,785 A | 1/1991 | Nayak |
| 4,981,786 A | 1/1991 | Dafforn et al. |
| 5,004,584 A | 4/1991 | Rayman |
| 5,006,464 A | 4/1991 | Chu et al. |
| 5,006,474 A | 4/1991 | Horstman et al. |
| 5,075,077 A | 12/1991 | Durley, III et al. |
| 5,087,556 A | 2/1992 | Ertinghausen |
| 5,091,153 A | 2/1992 | Bachand |
| 5,104,793 A | 4/1992 | Buck |
| 5,104,811 A | 4/1992 | Berger et al. |
| 5,110,550 A | 5/1992 | Schlipfenbacher |
| 5,132,208 A | 7/1992 | Freitag et al. |
| 5,137,808 A | 8/1992 | Ullman et al. |
| 5,147,780 A | 9/1992 | Pouletty et al. |
| 5,156,952 A | 10/1992 | Litman et al. |
| 5,162,238 A | 11/1992 | Eikmeier et al. |
| 5,169,789 A | 12/1992 | Bernstein |
| 5,173,433 A | 12/1992 | Bachand |
| 5,200,321 A | 4/1993 | Kidwell |
| 5,202,268 A | 4/1993 | Kuhn et al. |
| 5,217,905 A | 6/1993 | Marchand et al. |
| 5,219,762 A | 6/1993 | Katamine et al. |
| 5,223,436 A | 6/1993 | Freitag et al. |
| RE34,312 E | 7/1993 | Geiger et al. |
| 5,232,835 A | 8/1993 | Litman et al. |
| 5,238,649 A | 8/1993 | Nason |
| 5,240,735 A | 8/1993 | Lau |
| 5,244,631 A | 9/1993 | Morikawa |
| 5,244,788 A | 9/1993 | Hubscher |
| RE34,405 E | 10/1993 | Gould et al. |
| 5,275,785 A | 1/1994 | May et al. |
| 5,281,540 A | 1/1994 | Merkh et al. |
| 5,296,192 A | 3/1994 | Carroll et al. |
| 5,300,439 A | 4/1994 | Charlton |
| 5,306,623 A | 4/1994 | Kiser et al. |
| 5,308,775 A | 5/1994 | Donovan et al. |
| 5,332,548 A | 7/1994 | Moore |
| 5,334,502 A | 8/1994 | Sangha |
| 5,338,513 A | 8/1994 | Schlipfenbacher et al. |
| 5,340,748 A | 8/1994 | Baugher et al. |
| 5,356,782 A | 10/1994 | Moorman et al. |
| 5,362,654 A | 11/1994 | Pouletty |
| 5,369,007 A | 11/1994 | Kidwell |
| 5,384,264 A | 1/1995 | Chen et al. |
| 5,391,478 A | 2/1995 | Greene et al. |
| 5,399,316 A | 3/1995 | Yamada |
| 5,411,858 A | 5/1995 | McGeehan et al. |
| 5,418,136 A | 5/1995 | Miller et al. |
| 5,418,142 A | 5/1995 | Kiser et al. |
| 5,418,167 A | 5/1995 | Matner et al. |
| 5,424,215 A | 6/1995 | Albarella et al. |
| 5,424,220 A | 6/1995 | Goerlach-Graw et al. |
| 5,435,970 A | 7/1995 | Mamenta et al. |
| 5,451,504 A | 9/1995 | Fitzpatrick et al. |
| 5,468,648 A | 11/1995 | Chandler |
| 5,470,713 A | 11/1995 | El Shami et al. |
| 5,474,902 A | 12/1995 | Uylen et al. |
| 5,482,830 A | 1/1996 | Bogart et al. |
| 5,494,830 A | 2/1996 | Hubscher |
| 5,500,350 A | 3/1996 | Baker et al. |
| 5,501,985 A | 3/1996 | Baugher et al. |
| 5,514,557 A | 5/1996 | Moghaddam |
| 5,521,102 A | 5/1996 | Boehringer et al. |
| 5,532,133 A | 7/1996 | Barnwell |
| 5,541,057 A | 7/1996 | Bogart et al. |
| 5,550,063 A | 8/1996 | Bogart |
| 5,552,272 A | 9/1996 | Bogart |
| 5,558,834 A | 9/1996 | Chu et al. |
| 5,559,041 A | 9/1996 | Kang et al. |
| 5,567,594 A | 10/1996 | Calenoff |
| 5,571,667 A | 11/1996 | Chu et al. |
| 5,591,645 A | 1/1997 | Rosenstein |
| 5,602,040 A | 2/1997 | May et al. |
| 5,604,110 A | 2/1997 | Baker et al. |
| 5,607,863 A | 3/1997 | Chandler |
| 5,616,467 A | 4/1997 | Olsen et al. |
| 5,620,845 A | 4/1997 | Gould et al. |
| 5,622,871 A | 4/1997 | May et al. |
| 5,624,809 A | 4/1997 | Skold et al. |
| 5,629,164 A | 5/1997 | Rivers |
| 5,629,214 A | 5/1997 | Crosby |
| 5,639,671 A | 6/1997 | Bogart et al. |
| 5,641,639 A | 6/1997 | Perry |
| 5,648,274 A | 7/1997 | Chandler |
| 5,656,503 A | 8/1997 | May et al. |
| 5,658,801 A | 8/1997 | Poissant et al. |
| 5,670,381 A | 9/1997 | Jou et al. |
| 5,686,315 A | 11/1997 | Pronovost |
| 5,695,928 A | 12/1997 | Stewart |
| 5,695,930 A | 12/1997 | Weinstein et al. |
| 5,710,005 A | 1/1998 | Rittenburg |
| 5,714,341 A | 2/1998 | Thieme et al. |
| 5,714,389 A | 2/1998 | Charlton et al. |
| 5,723,345 A | 3/1998 | Yamauchi et al. |
| 5,726,010 A | 3/1998 | Clark |
| 5,728,587 A | 3/1998 | Kang et al. |
| 5,739,041 A | 4/1998 | Nazareth et al. |
| 5,750,333 A | 5/1998 | Clark |
| 5,766,961 A | 6/1998 | Pawlak et al. |
| 5,766,962 A | 6/1998 | Childs et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,807,756 A | 9/1998 | Bauman et al. |
| 5,814,522 A | 9/1998 | Zimmer et al. |
| 5,824,268 A | 10/1998 | Bernstein et al. |
| 5,827,646 A | 10/1998 | Middeldorp et al. |
| 5,846,838 A | 12/1998 | Chandler |
| 5,853,670 A | 12/1998 | Bunce |
| 5,861,265 A | 1/1999 | Perry |
| 5,869,272 A | 2/1999 | Bogart et al. |
| 5,869,345 A | 2/1999 | Chandler |
| 5,872,713 A | 2/1999 | Douglas et al. |
| 5,874,216 A | 2/1999 | Mapes |
| 5,877,028 A | 3/1999 | Chandler et al. |
| 5,879,951 A | 3/1999 | Sy |
| 5,885,526 A | 3/1999 | Chu |

| | | | | | |
|---|---|---|---|---|---|
| 5,885,527 A | 3/1999 | Buechler | 6,436,722 B1 | 8/2002 | Clark et al. |
| 5,891,650 A | 4/1999 | Godowski et al. | 6,455,324 B1 | 9/2002 | Douglas |
| 5,900,379 A | 5/1999 | Noda et al. | 6,472,226 B1 | 10/2002 | Barradine et al. |
| 5,902,722 A | 5/1999 | Di Cesare et al. | 6,475,805 B1 | 11/2002 | Charm et al. |
| 5,912,116 A | 6/1999 | Caldwell | 6,485,982 B1 | 11/2002 | Charlton |
| 5,922,533 A | 7/1999 | Vallari et al. | 6,489,129 B1 | 12/2002 | Faatz et al. |
| 5,922,615 A | 7/1999 | Nowakowski et al. | 6,492,127 B2 | 12/2002 | Goodell et al. |
| 5,939,252 A | 8/1999 | Lennon et al. | 6,500,629 B1 | 12/2002 | Cleaver et al. |
| 5,939,272 A | 8/1999 | Buechler et al. | 6,503,702 B1 | 1/2003 | Stewart |
| 5,948,695 A | 9/1999 | Douglas et al. | 6,503,722 B1 | 1/2003 | Valkirs |
| 5,955,377 A | 9/1999 | Maul et al. | 6,511,814 B1 | 1/2003 | Carpenter |
| 5,958,790 A | 9/1999 | Cerny | 6,514,769 B2 | 2/2003 | Lee |
| 5,965,458 A | 10/1999 | Kouvonen et al. | 6,514,773 B1 | 2/2003 | Klein et al. |
| 5,972,720 A | 10/1999 | Nichtl et al. | 6,528,321 B1 | 3/2003 | Fitzgerald et al. |
| 5,976,895 A | 11/1999 | Cipkowski | 6,528,322 B1 | 3/2003 | Carlsson et al. |
| 5,985,675 A | 11/1999 | Charm et al. | 6,528,323 B1 | 3/2003 | Thayer et al. |
| 5,989,921 A | 11/1999 | Charlton et al. | 6,528,325 B1 | 3/2003 | Hubscher et al. |
| 5,998,220 A | 12/1999 | Chandler | 6,534,324 B1 | 3/2003 | Zin |
| 5,998,221 A | 12/1999 | Malick et al. | 6,544,474 B2 | 4/2003 | Douglas |
| 6,008,056 A | 12/1999 | Thieme | 6,548,309 B1 | 4/2003 | Moore et al. |
| 6,017,767 A | 1/2000 | Chandler | 6,551,842 B1 | 4/2003 | Carpenter |
| 6,027,890 A | 2/2000 | Ness et al. | 6,592,815 B1 | 7/2003 | Zimmer |
| 6,040,195 A | 3/2000 | Carroll et al. | 6,593,085 B1 | 7/2003 | Barnett et al. |
| 6,046,013 A | 4/2000 | Tidey et al. | 6,602,719 B1 | 8/2003 | Carpenter |
| 6,046,057 A | 4/2000 | Nazareth et al. | 6,617,116 B2 | 9/2003 | Guan et al. |
| 6,057,166 A | 5/2000 | Childs et al. | 6,623,955 B2 | 9/2003 | Matner et al. |
| 6,060,326 A | 5/2000 | Frank et al. | 6,627,459 B1 | 9/2003 | Tung et al. |
| 6,063,337 A | 5/2000 | Markart | 6,632,681 B1 | 10/2003 | Chu |
| 6,087,184 A | 7/2000 | Magginetti et al. | 6,645,732 B2 | 11/2003 | Faatz et al. |
| 6,106,732 A | 8/2000 | Johnston et al. | 6,649,418 B1 | 11/2003 | Geisberg |
| 6,140,134 A | 10/2000 | Rittenburg | 6,656,744 B2 | 12/2003 | Pronovost et al. |
| 6,140,136 A | 10/2000 | Lee | 6,656,745 B1 | 12/2003 | Cole |
| 6,168,956 B1 | 1/2001 | Chandler | 6,660,469 B1 | 12/2003 | Wright et al. |
| 6,187,268 B1 | 2/2001 | Albarella et al. | 6,663,833 B1 | 12/2003 | Stave et al. |
| 6,187,598 B1 | 2/2001 | May et al. | 6,673,628 B2 | 1/2004 | Freitag et al. |
| 6,194,220 B1 | 2/2001 | Malick et al. | RE38,430 E | 2/2004 | Rosenstein |
| 6,197,494 B1 | 3/2001 | Oberhardt | 6,686,167 B2 | 2/2004 | Bagaria |
| 6,221,625 B1 | 4/2001 | Ashihara et al. | 6,699,722 B2 | 3/2004 | Bauer et al. |
| 6,221,678 B1 | 4/2001 | Chandler | 6,703,196 B1 | 3/2004 | Klepp et al. |
| 6,224,831 B1 | 5/2001 | Stafford et al. | 6,706,539 B2 | 3/2004 | Nelson et al. |
| 6,228,660 B1 | 5/2001 | May et al. | 6,713,309 B1 | 3/2004 | Anderson et al. |
| 6,235,464 B1 | 5/2001 | Henderson et al. | 6,727,073 B1 | 4/2004 | Moore et al. |
| 6,248,598 B1 | 6/2001 | Bogema | 6,737,277 B1 | 5/2004 | Kang et al. |
| 6,258,548 B1 | 7/2001 | Buck | 6,750,031 B1 | 6/2004 | Ligler et al. |
| 6,271,040 B1 | 8/2001 | Buechler | 6,753,190 B1 | 6/2004 | Okada et al. |
| 6,271,045 B1 | 8/2001 | Douglas et al. | 6,767,710 B2 | 7/2004 | DiNello et al. |
| 6,271,046 B1 | 8/2001 | Chandler | 6,767,714 B2 | 7/2004 | Nazareth et al. |
| 6,277,650 B1 | 8/2001 | Nazareth et al. | 6,780,651 B2 | 8/2004 | Douglas et al. |
| 6,284,550 B1 | 9/2001 | Carroll et al. | 6,790,611 B2 | 9/2004 | Lassen et al. |
| 6,287,875 B1 | 9/2001 | Geisberg | 6,797,481 B1 | 9/2004 | Ullman et al. |
| 6,297,020 B1 | 10/2001 | Brock | 6,808,889 B2 | 10/2004 | Fitzpatrick et al. |
| 6,297,060 B1 | 10/2001 | Nowakowski et al. | 6,808,937 B2 | 10/2004 | Ligler et al. |
| 6,300,142 B1 | 10/2001 | Andrewes et al. | 6,812,038 B1 | 11/2004 | Mendel-Hartvig et al. |
| RE37,437 E | 11/2001 | Friesen et al. | 6,818,180 B2 | 11/2004 | Douglas et al. |
| 6,316,205 B1 | 11/2001 | Guan et al. | 6,818,455 B2 | 11/2004 | May et al. |
| 6,316,264 B1 | 11/2001 | Corey et al. | 6,824,975 B2 | 11/2004 | Hubscher et al. |
| 6,319,676 B1 | 11/2001 | Nazareth et al. | 6,824,997 B1 | 11/2004 | Moore et al. |
| 6,326,214 B1 | 12/2001 | Liu et al. | 6,828,110 B2 | 12/2004 | Lee et al. |
| 6,335,205 B1 | 1/2002 | Bausback | RE38,688 E | 1/2005 | Friesen et al. |
| 6,352,862 B1 | 3/2002 | Davis et al. | 6,844,200 B2 | 1/2005 | Brock |
| 6,362,008 B1 | 3/2002 | Kohn et al. | 6,846,635 B1 | 1/2005 | Anderson et al. |
| 6,368,875 B1 | 4/2002 | Geisberg | 6,849,414 B2 | 2/2005 | Guan et al. |
| 6,368,876 B1 | 4/2002 | Huang et al. | 6,855,561 B2 | 2/2005 | Jerome et al. |
| 6,372,514 B1 | 4/2002 | Lee | 6,863,866 B2 | 3/2005 | Kelly et al. |
| 6,372,515 B1 | 4/2002 | Casterlin et al. | 6,867,051 B1 | 3/2005 | Anderson et al. |
| 6,372,516 B1 | 4/2002 | Sun | 6,887,701 B2 | 5/2005 | Anderson et al. |
| 6,376,195 B1 | 4/2002 | Mapes | 6,905,835 B2 | 6/2005 | Sorell Gomez et al. |
| 6,399,398 B1 | 6/2002 | Cunningham et al. | 6,924,153 B1 | 8/2005 | Boehringer et al. |
| 6,403,383 B1 | 6/2002 | Casterlin et al. | 6,927,068 B2 | 8/2005 | Simonson et al. |
| 6,403,384 B1 | 6/2002 | Lea | 6,991,940 B2 | 1/2006 | Carroll et al. |
| 6,406,922 B2 | 6/2002 | Casterlin et al. | 7,018,847 B2 | 3/2006 | Mendel-Hartvig et al. |
| 6,413,473 B1 | 7/2002 | Bacon | 7,045,342 B2 | 5/2006 | Nazareth et al. |
| 6,413,784 B1 | 7/2002 | Lundsgaard et al. | 7,049,130 B2 | 5/2006 | Carroll et al. |

| Patent/Publication | Date | Name |
|---|---|---|
| 7,109,042 B2 | 9/2006 | May et al. |
| 7,189,522 B2 * | 3/2007 | Esfandiari ............ 435/7.1 |
| 7,270,995 B2 | 9/2007 | Matsushita et al. |
| 7,682,801 B2 * | 3/2010 | Esfandiari ............ 435/7.1 |
| 2001/0012637 A1 | 8/2001 | Casterlin et al. |
| 2001/0026942 A1 | 10/2001 | Carpenter et al. |
| 2001/0026944 A1 | 10/2001 | Chung et al. |
| 2001/0034068 A1 | 10/2001 | Spivey et al. |
| 2001/0039057 A1 | 11/2001 | Douglas et al. |
| 2001/0048893 A1 | 12/2001 | Norris et al. |
| 2002/0001853 A1 | 1/2002 | Obremski et al. |
| 2002/0015663 A1 | 2/2002 | Goldstein et al. |
| 2002/0019062 A1 | 2/2002 | Lea et al. |
| 2002/0031839 A1 | 3/2002 | McNeirney et al. |
| 2002/0046614 A1 | 4/2002 | Alley |
| 2002/0048819 A1 | 4/2002 | Alley |
| 2002/0052050 A1 | 5/2002 | Douglas et al. |
| 2002/0057991 A1 | 5/2002 | Kelly et al. |
| 2002/0058330 A1 | 5/2002 | Carroll et al. |
| 2002/0110803 A1 | 8/2002 | Dhar et al. |
| 2002/0119497 A1 | 8/2002 | Wild et al. |
| 2002/0142291 A1 | 10/2002 | Bauer et al. |
| 2002/0155028 A1 | 10/2002 | Wong |
| 2002/0173050 A1 | 11/2002 | DiNello et al. |
| 2002/0192839 A1 | 12/2002 | Mink et al. |
| 2003/0045001 A1 | 3/2003 | Burgess et al. |
| 2003/0118480 A1 | 6/2003 | Kaylor et al. |
| 2003/0124740 A1 | 7/2003 | Bachand |
| 2003/0138351 A1 | 7/2003 | Etes et al. |
| 2003/0143639 A1 | 7/2003 | Matsushita et al. |
| 2003/0180967 A1 | 9/2003 | Shigetoh |
| 2004/0087036 A1 | 5/2004 | Chung et al. |
| 2004/0142495 A1 | 7/2004 | Hartman et al. |
| 2004/0161859 A1 | 8/2004 | Guo et al. |
| 2004/0184954 A1 | 9/2004 | Guo et al. |
| 2004/0219694 A1 | 11/2004 | Chittock et al. |
| 2004/0235189 A1 | 11/2004 | Lu |
| 2004/0241779 A1 | 12/2004 | Piasio et al. |
| 2004/0248322 A1 | 12/2004 | Charlton |
| 2005/0074900 A1 | 4/2005 | Morgan et al. |
| 2005/0079629 A1 | 4/2005 | Guo et al. |
| 2005/0112779 A1 | 5/2005 | Wei et al. |
| 2005/0112780 A1 | 5/2005 | Song |
| 2005/0112782 A1 | 5/2005 | Buechler |
| 2005/0130293 A1 | 6/2005 | Blatt et al. |
| 2005/0130319 A1 | 6/2005 | Biegelsen et al. |
| 2005/0136500 A1 | 6/2005 | Yang et al. |
| 2005/0142032 A1 | 6/2005 | Hoenes et al. |
| 2005/0164404 A1 | 7/2005 | Marlborugh et al. |
| 2005/0170527 A1 | 8/2005 | Boehringer et al. |
| 2005/0208677 A1 | 9/2005 | Owens et al. |
| 2005/0227371 A1 | 10/2005 | Gokhan |
| 2005/0244985 A1 | 11/2005 | Freitag et al. |
| 2005/0244986 A1 | 11/2005 | May et al. |
| 2006/0099719 A1 | 5/2006 | Curcio |
| 2006/0121626 A1 | 6/2006 | Imrich |
| 2006/0134803 A1 | 6/2006 | Esfandiari |

* cited by examiner

TB STAT-PAK II vs. NEW GENERATION TB ASSAY

SAMPLES: TBGL CONTROLS

| | TB STAT-PAK™ II | NEW GENERATION |
|---|---|---|
| 32 U/ml | +++ | +++ |
| 8 U/ml | ++ | ++ |
| 2 U/ml | +/− | + |
| 1 U/ml | − | + |
| 1/2 U/ml | − | + |
| 1/4 U/ml | − | + |
| 1/8 U/ml | − | − |
| 0 U/ml | − | − |

NOTE: DILUTIONS ≤ 1 U/ml WERE MADE FROM 2 U/ml SAMPLE

FIG. 11

LABORATORY RESULT FOR THE NEW GENERATION HIV TEST

|  | DILUTION | NG HIV TEST | HIV STAT-PAK™ |
|---|---|---|---|
| HIV-1 | 1:64 | 3 | 3 |
|  | 1:128 | 3 | 2 |
|  | 1:256 | 3 | 3 |
|  | 1:512 | 2 | 2 |
|  | 1:1024 | 1 | 1 |
|  | 1:2048 | 1 | N |
|  | 1:4096 | 1 | N |
|  | 1:8192 | N | N |
| HIV-2 | 1:4 | 3 | 3 |
|  | 1:8 | 3 | 3 |
|  | 1:16 | 3 | 2 |
|  | 1:32 | 2 | 2 |
|  | 1:64 | 2 | 1 |
|  | 1:128 | 2 | 1 |
|  | 1:256 | 2 | N |
|  | 1:512 | 1 | N |
|  | 1:1024 | N | N |
|  | 1:2048 | N | N |

INTENSITY     RESULT

1 —  WEAK POS
2 —  MEDIUM POS
3 —  STRONG POS
N —  NEGATIVE

FIG.12

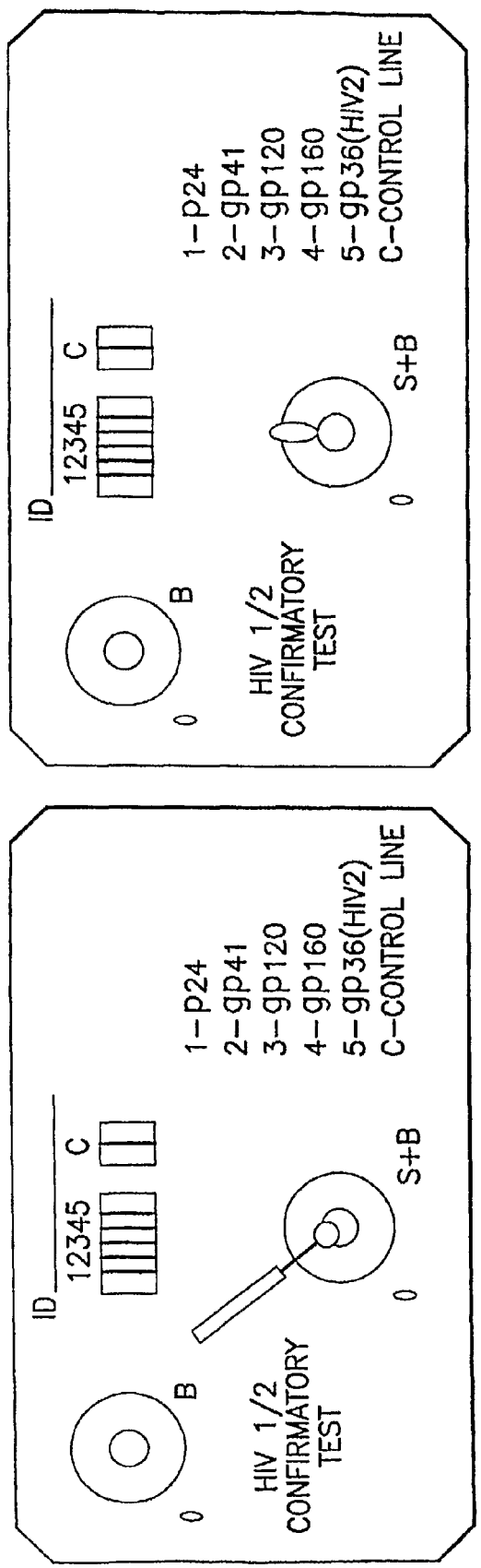

3. ADD 3 DROPS (90 μl) OF BUFFER TO THE BUFFER WELL (B) WHEN THE COLORED LINES DISAPPEAR COMPLETELY

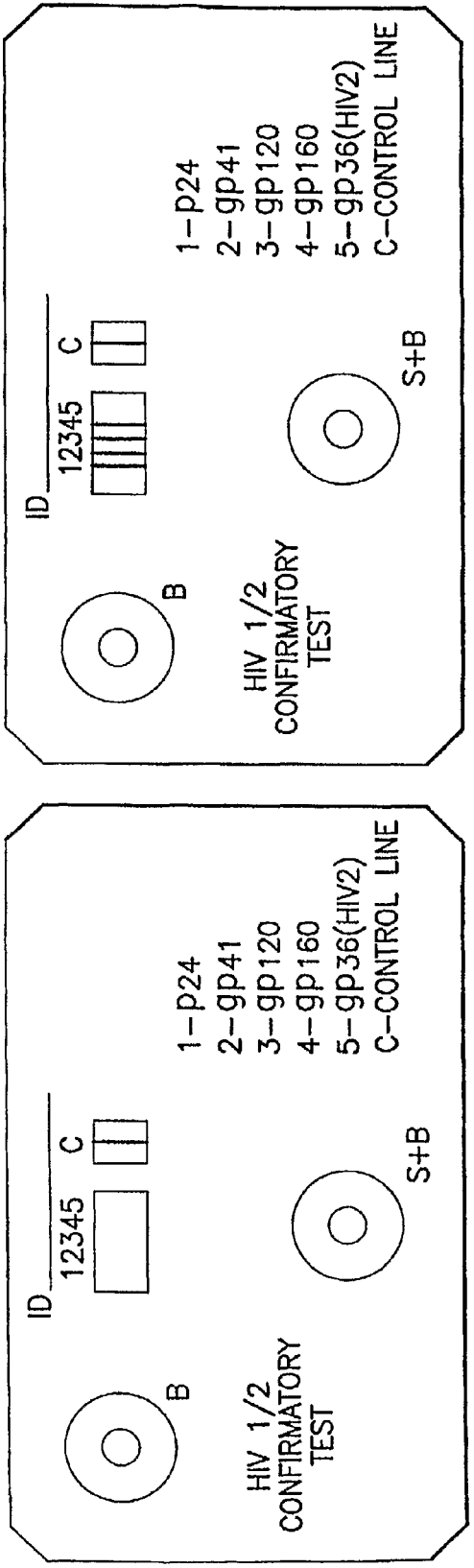

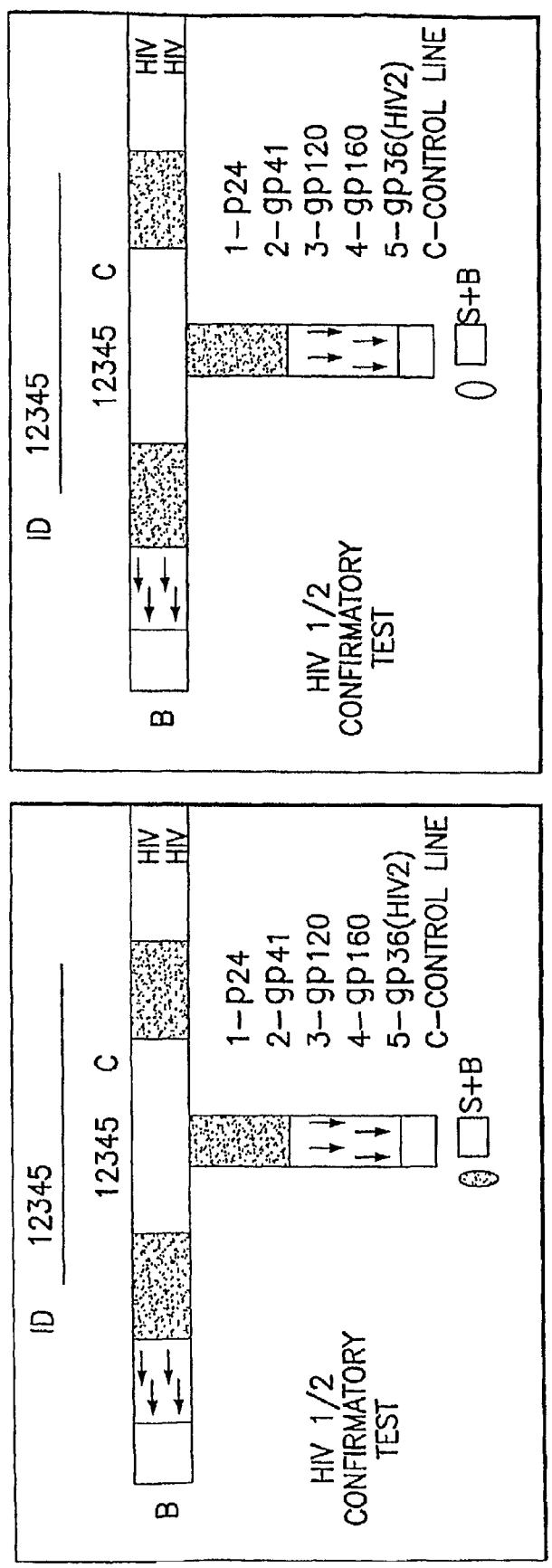

NEGATIVE RESULT

HIV1 POSITIVE RESULT
(AT LEAST TWO HIV1 ANTIGENS REACTIVE)

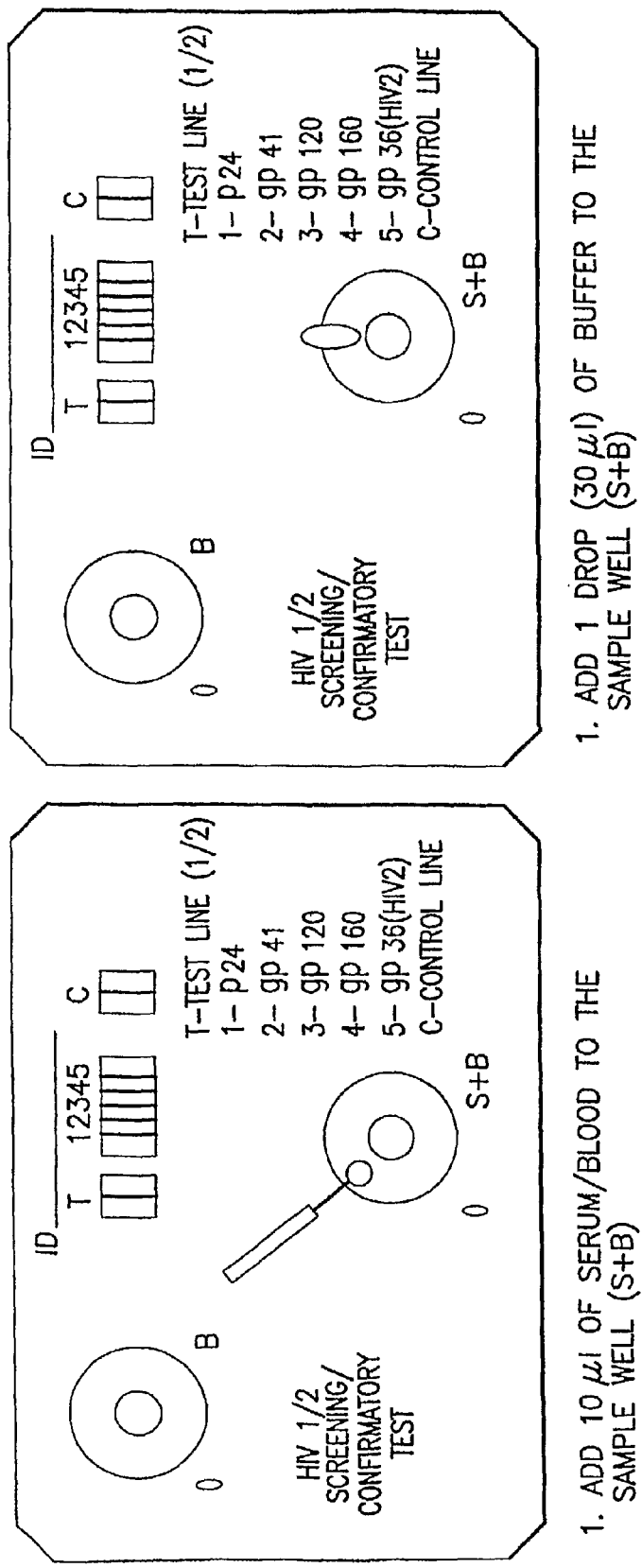

US 7,879,597 B2

DUAL PATH IMMUNOASSAY DEVICE

This application is a 371 of PCT/US 06/08688 filed 10 Mar. 2006 which claims benefit of U.S. Ser. No. 60/660,695 filed 11 Mar. 2005, and claims benefit of U.S. Ser. No. 60/680,884 filed 13 May 2005, and claims benefit of U.S. Ser. No. 60/741,628 filed 2 Dec. 2005. This application is also a continuation-in-part of and claims priority from U.S. Ser. No. 11/172,298 filed 30 Jun. 2005.

BACKGROUND OF THE INVENTION

1. Field of the Invention

This invention relates broadly to immunoassay devices and the methods for their use. More particularly, this invention relates to chromatographic rapid test strips for detection of a ligand in a body fluid.

2. State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Even the qualitative assays must be very sensitive because of the often small concentration of the ligand of interest in the test fluid. False positives can also be troublesome, particularly with agglutination and other rapid detection methods such as dipstick and color change tests. Because of these problems, so-called "sandwich" assays and other sensitive detection mechanisms which use metal sols or other types of colored particles have been developed.

In a "sandwich" assay, a target analyte such as an antigen is "sandwiched" between a labeled antibody and an antibody immobilized onto a solid support. The assay is read by observing the presence and/or amount of bound antigen-labeled antibody complex. In a "competition" immunoassay, antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample.

Because these and other assays can detect both antibodies and antigens, they are generally referred to as immunochemical ligand-receptor assays or simply immunoassays.

Solid phase immunoassay devices, whether of the sandwich or competition type, provide sensitive detection of an analyte in a biological fluid sample such as blood, urine, or saliva. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. In the last decade, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design.

In the more common forms of dipstick assays, as typified by home pregnancy and ovulation detection kits, immunochemical components such as antibodies are bound to a solid phase. The assay device is "dipped" for incubation into a sample suspected of containing unknown antigen analyte. Enzyme-labeled antibody is then added, either simultaneously or after an incubation period. The device is then washed and inserted into a second solution containing a substrate for the enzyme. The enzyme-label, if present, interacts with the substrate, causing the formation of colored products which either deposit as a precipitate onto the solid phase or produce a visible color change in the substrate solution.

Flow-through type immunoassay devices were designed to obviate the need for extensive incubation and cumbersome washing steps associated with dipstick assays. Valkirs et al., U.S. Pat. No. 4,632,901, disclose a device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane which acts as a reagent delivery system.

The requirement of multiple addition and washing steps with dipstick and flow-through type immunoassay devices increases the likelihood that minimally trained personnel and home users will obtain erroneous assay results.

In migration type assays, a membrane is impregnated with the reagents needed to perform the assay. An analyte detection zone is provided in which labeled analyte is bound and assay indicia is read. See, for example, Tom et al., U.S. Pat. No. 4,366,241, and Zuk, et al. U.S. Pat. No. 4,596,275. The sensitivity of migration type assays is frequently reduced, however, by the presence or formation in the sample of undesirable solid components which block the passage of labeled analyte to the detection zone. Assay sensitivity also declines when migration assay devices are flooded with too much liquid sample.

Migration assay devices usually incorporate within them reagents which have been attached to colored labels (i.e., conjugates), thereby permitting visible detection of the assay results without addition of further substances. See, for example, Bernstein, U.S. Pat. No. 4,770,853. Among such labels are gold sol particles such as those described by Leuvering in U.S. Pat. No. 4,313,734, dye sol particles such as described in U.S. Pat. No. 4,373,932 by Gribnau et al., dyed latex such as described by May et al., WO 88/08534, and dyes encapsulated in liposomes by Campbell et al., U.S. Pat. No. 4,703,017. These colored labels are generally limited in terms of the immobilization methods which are suitable. Moreover, they require a relatively large amount of ligand molecule and can involve expensive reagents, thereby adding to the cost. Thus, there still remains a need for extremely reliable but inexpensive rapid detection devices. There also still remains a need for a highly sensitive assay which can utilize a small sample volume while providing accurate results.

SUMMARY OF THE INVENTION

It is therefore an object of the invention to provide a rapid detection immunoassay device.

It is another object of the invention to provide immunoassay devices which are simple to use and provide accurate results.

It is a further object of the invention to provide immunoassay devices which do not require migration of analytes along the same path as conjugate carrying buffer solutions.

It is also an object of the invention to provide rapid detection immunoassay devices which are simple in construction.

It is an additional object of the invention to provide immunoassay devices which can use either a dry or liquid conjugate system.

Another object of the invention is to provide a highly sensitive immunoassay device which provides accurate results while using small sample volumes.

A further object of the invention is to provide highly sensitive immunoassay devices which are useful with different types of body fluids.

In accord with these objects, which will be discussed in detail below, both dry and liquid conjugate immunoassay device systems are provided. The systems of the invention include test cells with a first sorbent material having a first location for receiving a buffer solution (in the case of a dry conjugate system) or a conjugate solution (in the case of a liquid conjugate system) with the first sorbent material defining a first horizontal flow path, a second sorbent material having a second location for receiving a sample with the second sorbent material defining a second horizontal flow path distinct from the first flow path, and a test line or test site with immobilized antigens or antibodies or other ligand binding molecules such as aptamers, nucleic acids, etc. located in a test zone at a junction of the first and second sorbent materials. For purposes herein, the term "distinct" when used in conjunction with the words "flow path" or "migration path" shall be understood to mean "not in fluid communication except via a test zone".

Where the test cell of the invention is provided in a housing, the housing is provided with a first opening adjacent the first location and a second opening adjacent the second location. A viewing window is provided in the housing above the test line.

In the preferred embodiment of the invention, the first sorbent material and second sorbent material are separate pieces which overlie one another and the test line is printed on one or both of the sorbent materials at the junction. Alternatively, although not preferred, the first and second sorbent materials can be integral with each other. The systems of the invention preferably also include a control line or site which may be seen from the viewing window.

According to one set of embodiments of the invention, the sorbent materials of the invention (and the housing in which the materials are provided) are laid out in a T shape, where the first location for receiving the buffer or buffer-conjugate solution is located near one end of the top bar of the T, the second location for receiving the sample is located near the end of the stem of the T, and the sorbent materials overlie each other at the intersection. According to another set of embodiments of the invention, the sorbent materials of the invention (and the housing in which the materials are provided) take a + shape, where the first location for receiving the buffer or buffer-conjugate solution is located near one end of a first bar, the second location for receiving the sample is located near the end of one end of the second bar, and the sorbent materials overlie each other at the intersection. Of course, the sorbent materials may be laid out in other configurations, and the housing may take other shapes, such as rectangular, square, irregular, etc. regardless of the manner in which the sorbent materials are arranged.

In one embodiment of the invention, the materials, thicknesses and lengths of the first and second sorbent materials are chosen to adjust the timing regarding the liquid sample and liquid buffer reaching the test site.

In the dry conjugate system of the invention, a dry conjugate is provided between the first opening and the test site. The conjugate is supported on or within the sorbent material such that when a buffer is added in the first opening, the sorbent material wicks the buffer to the conjugate which is then carried by the buffer to the test site. In the liquid conjugate system of the invention, a buffer-conjugate liquid subsystem is provided and applied to the first opening. The sorbent material then wicks the buffer-conjugate subsystem to the test site.

According to one method of the invention, a system is provided which includes a test cell having a first sorbent material having a first location for receiving a buffer solution (in the case of a dry conjugate system) or a conjugate solution (in the case of a liquid conjugate system) with the first sorbent material defining a first horizontal flow path, a second sorbent material having a second location for receiving a sample with the second sorbent material defining a second horizontal flow path distinct from the first flow path, and a test line or test site with immobilized antigens or antibodies or other ligand binding molecules such as aptamers, nucleic acids, etc. located in a test zone at a junction of the first and second sorbent materials. If desired, a housing is also provided having a first opening for receiving the buffer or conjugate solution, a second opening for receiving a sample, and a viewing window above the test line. A sample of interest is provided to the second opening or location. After a desired amount of time, a liquid such as a buffer solution is added to the first opening or location. If the sorbent material is supporting a conjugate (i.e., in a dry conjugate system), the liquid is preferably simply a buffer solution. If the sorbent material is not supporting a conjugate (i.e., in a liquid conjugate system), the liquid is preferably a buffer-conjugate liquid subsystem. In any event, after sufficient time to permit the conjugate to migrate to the test site (and control site if provided), the test site (and control site if provided) is inspected in order to determine whether the sample is "positive" or not.

It will be appreciated that the system of the invention can be used in conjunction with different types of samples such as blood, urine, saliva, and feces, and can be used to test for the presence of any ligand. Where blood, saliva or feces is to be provided, the blood, saliva or feces may be diluted or mixed with buffer prior to being added through the second hole. Alternatively, in some cases, the sample may be added through the hole and then a diluent may be added through the same hole.

The test cell of the invention is advantageous over the prior art because the test cell of the invention overcomes aggregation/agglutination problems between the conjugate and the analyte in the sample which is a significant problem in traditional chromatographic immunoassay for relatively large analytes such as bacteria. In particular, in traditional chromatographic immunoassays, the complex between bacteria and conjugated antibody has difficulty migrating to the test line and tends to remain in the bottom of test strip or in the pad. In this invention there is no complex binding between analyte and the conjugate until the sample reaches the test site, as the analyte is applied via its own path to the test site while the conjugate migrates by itself. As a result, the system of the invention is extremely sensitive and specific.

Additional objects and advantages of the invention will become apparent to those skilled in the art upon reference to the detailed description taken in conjunction with the provided figures.

BRIEF DESCRIPTION OF THE DRAWINGS

FIG. 11 is a table showing a comparison of the sensitivity of the test device of the invention relative to a typical prior art TB test device.

FIG. 12 includes two tables and a key, with the tables showing comparisons of the sensitivity of the test device of the invention relative to typical prior art HIV1 and HIV2 test devices.

FIGS. 13A-13G are composite photograph/instructional diagrams of an HIV 1/2 test cassette product according to the invention with FIGS. 13A-13C showing the procedure of utilizing the test product, and FIGS. 13D-13G showing various possible results.

FIGS. 14A-14G are composite photograph/instructional diagrams of an HIV 1/2 dipstick test product according to the invention with FIGS. 14A-14C showing the procedure of utilizing the test product, and FIGS. 14D-14G showing various possible results.

FIGS. 15A-15G are composite photograph/instructional diagrams of an HIV1/2 screening/confirmatory test cassette product according to the invention with FIGS. 15A-15C showing the procedure utilizing the screening/test product, and FIGS. 15D-15G showing various possible results.

DETAILED DESCRIPTION OF THE PREFERRED EMBODIMENTS

Figure 1:
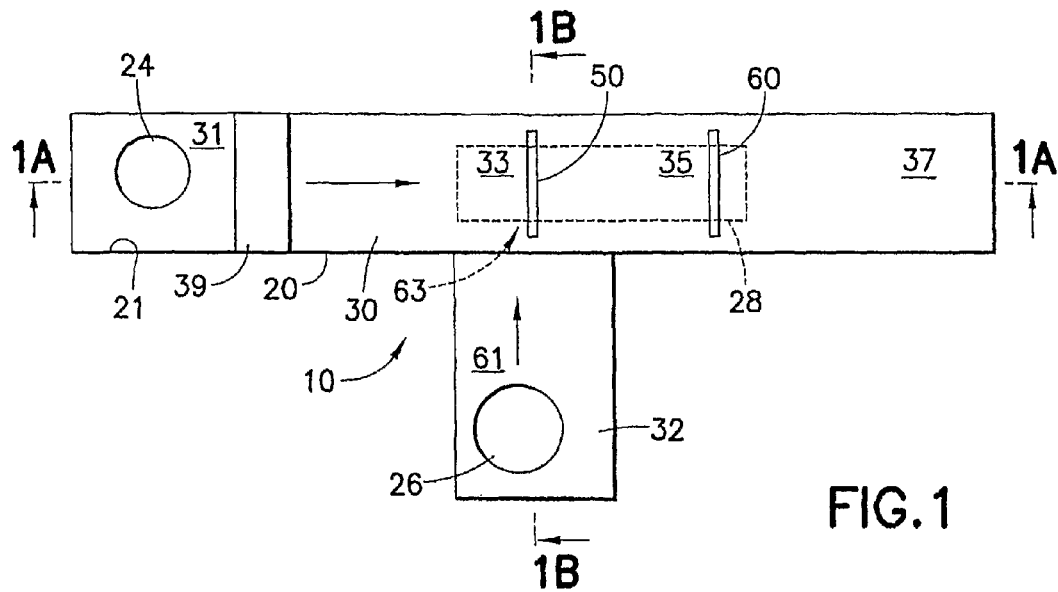
FIG. 1 is a top schematic view of a first embodiment of the invention.
Figure 1A:
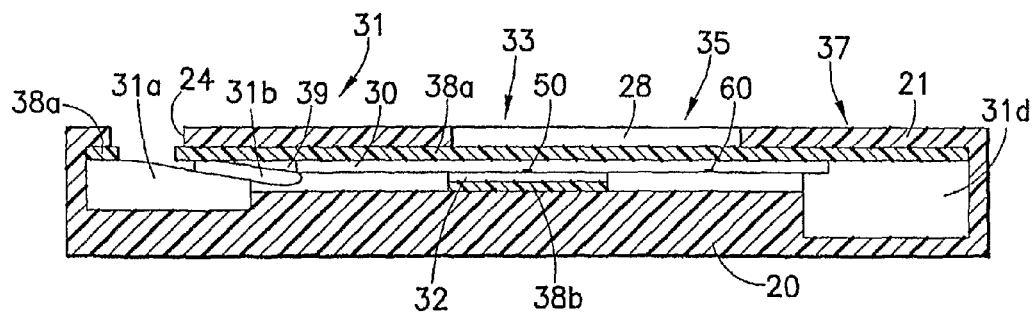
FIG. 1A is a cross-sectional view taken along line 1A-1A of FIG. 1.
Figure 1B:
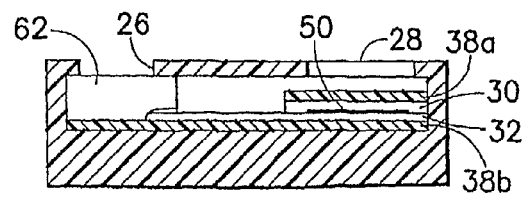
FIG. 1B is a cross-sectional view taken along line 1B-1B of FIG. 1.

Turning now to FIGS. 1, 1A and 1B, an immunoassay device test cell 10 is provided and includes: a T-shaped housing 20 having a top wall 21 defining first and second holes 24, 26, and a window 28; and first and second sorbent or bibulous materials 30, 32 defining perpendicular horizontal flow paths in the housing. The first sorbent material 30 includes at least two and preferably three or four zones and may be made from a plurality of materials. A first zone 31 (sometimes called a filter zone) is located at the first hole 24 and extends to a second zone 33 (sometimes called a test zone) which is located at the junction of the "T". The first zone 31 preferably includes a filter 31a, a pad 31b on or in which a conjugate 39 having desired antigens or antibodies with attached colored markers is deposited and immobilized, and a first portion of a thin membrane or sorbent or bibulous material 30 typically made from nitrocellulose with a plastic backing (not shown). The first zone 31 is adapted to receive a buffer solution, to cause the buffer solution to contact the conjugate, thereby mobilizing the conjugate, and to wick the conjugate-carrying buffer solution to the second zone 33. The second (test) zone 33 includes a second portion of the thin membrane 30 which is preferably printed with a test line 50 having immobilized antigens or antibodies (depending on whether the test cell is designed to test for the presence of antibodies or antigens) on the membrane as is well known in the art. The test line 50 may be seen through the window 28 of clear plastic provided in the housing. An optional third zone 35 (sometimes called a control zone) which includes a third portion of the thin membrane 30 may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, window 28 extends above the control line 60. If desired, an optional fourth zone 37 (sometimes called a reservoir zone) may be provided as a wicking reservoir as is also well known in the art. The fourth zone 37 includes a relatively thicker absorbent paper 31d. Preferably overlying all the zones is a thin, preferably transparent plastic film or card 38a having an adhesive which keeps the sorbent materials in place. The card 38a may be cut with an opening at hole 24 so that it does not block liquid access to the hole 24.

The second sorbent material 32 may also be made from a plurality of materials and preferably includes two zones 61, 63. The first zone 61 (sometimes called a filter zone) includes a filter or pad 62 and a first portion of a thin membrane or sorbent or bibulous material 32 typically made from nitrocellulose with a backing (not shown). The first zone 61 is located at the second hole 26 and extends to the second zone 63. The second zone 63 includes a second portion of the thin membrane 32 which is in contact with the second zone 33 of the first sorbent material 30. As is seen in FIGS. 1A and 1B, the first sorbent material 30 overlies the second sorbent material 32 such that the membranes are in contact with each other (as opposed to the backings contacting the membranes or each other), and such that the test line 50 is effectively located between the membranes. Thus, test line 50 could be printed on the second zone 63 of the second sorbent material 32 instead of, or in addition to the second zone 33 of the first sorbent material 30. If desired, a thin plastic film or card 38b having an adhesive which keeps the second sorbent material in place may be utilized.

Where standard-type nitrocellulose strips with a backing are utilized as the first and second membranes, it is desirable for the membranes to have different pore sizes. For example, and as discussed in more detail hereinafter, if membrane 31 (for the conjugate migration) has a 3μ pore size, and membrane 32 (for the sample migration) has a 15μ pore size, sample applied to membrane 32 will tend to migrate and stay in the sample membrane 32 and will tend not to migrate into the conjugate membrane 31.

The immunoassay of FIG. 1 is preferably utilized as follows. First, a sample (not shown) possibly containing antibodies (or antigens) is provided to the second opening or hole 26 and allowed to migrate through the second sorbent material 32 to its second zone 63 which is contact with the second zone 33 of the first sorbent material 30. Optionally, after providing the sample to hole 26, a preferably measured amount of liquid such as a buffer solution may be added to hole 26 to help in the migration of the sample. Regardless, the sample reaches the test line 50 which is printed atop the second zone 33 of the first sorbent material or infused therein. After a desired amount of time, by which time the antibodies (or antigens) in the sample (if present) will have had an opportunity to bind to the antigens (or antibodies) immobilized at the test line 50, a preferably measured amount of liquid such as a buffer solution (not shown) is added to the first opening 24. After another period of time, sufficient to permit the conjugate to migrate to the test site 50 (and control site 60 if provided), the test site 50 (and control site 60 if provided) is inspected via window 28 in order to determine whether the sample is "positive" or not. Typically, a "positive" test indicating the presence of the antibody (or antigen) in the sample is obtained when both the test site 50 and the control site 60 show lines of color. A "negative" test indicating the lack of the presence of the antibody (or antigen) in the sample is obtained when only the control site 60 shows a line of color.

The method of the invention may be expedited by providing the housing with numbering and/or lettering to indicate that hole 26 is for receiving the sample (and optionally some buffer) and is to be used first, and that hole 24 is for receiving the buffer solution and is to be used second.

Those skilled in the art will appreciate that the immunoassay 10 functions as follows. Because the test line 50 is provided with antigens (or antibodies) immobilized on a membrane, if the test sample contains antibodies to the antigens (or antigens to the antibodies), the antibodies (or antigens) will bind themselves to the antigens (or antibodies) at the test line. Thereafter, when the conjugate 39 containing an antigen for the antibody (or antibody for the antigen) coupled to a colored marker is caused to migrate to the test line, if the test sample contains the antibodies (or antigens) which are now held at the test line 50, the antigen (or antibody) of the conjugate will bind itself to the antibodies (or antigens) and the colored marker will cause a colored line to appear at the test site 50. If the test sample does not contain antibodies (or antigens), the conjugate will not have the antibodies (antigens) to bind to at the test line 50, and no colored line will appear at the test site 50. On the other hand, because the control line 60 is provided with antibodies (or antigens), the antigens (or antibodies) of the conjugate will always bind to the antibodies (or antigens) in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

Figure 2:
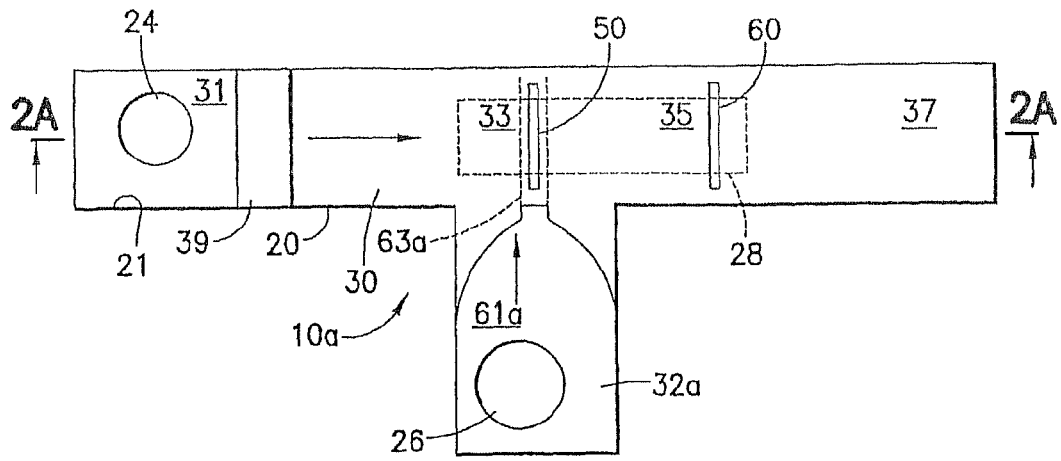
FIG. 2 is a top schematic view of a second embodiment of the invention.
Figure 2A:
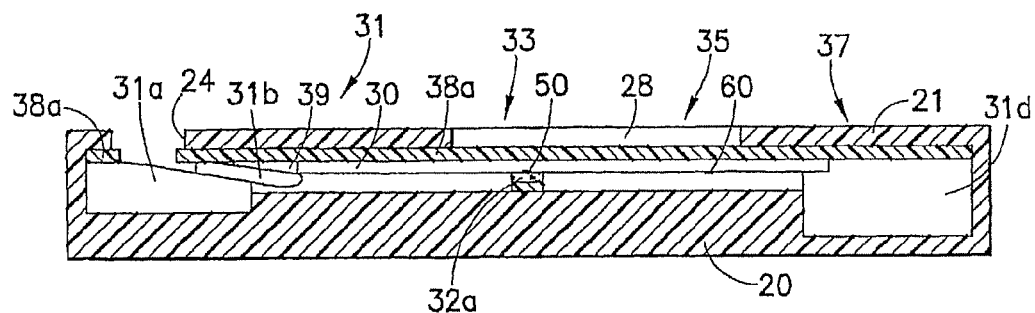
FIG. 2A is a cross-sectional view taken along line 2A-2A of FIG. 2.

Turning now to FIG. 2 and FIG. 2A, a second embodiment of the invention is seen. In FIGS. 1, 1A, 1B, 2 and 2A, like numbers are used for like elements. Thus, it will be appreciated that the primary difference between the second embodiment of FIGS. 2 and 2A and the first embodiment of FIGS. 1, 1A, and 1B is that the second sorbent material 32a of test cell 10a is key-shaped (preferably via punching). With the key-shaped arrangement, zone 61a is shaped so that it converges to the second narrow zone 63a. As a result, zone 63a touches the second zone 33 of the first sorbent material 30 almost exclusively at the location of the test line 50. Those skilled in the art will appreciate that the immunoassay test cell 10a of FIG. 2 may be used in the same manner and functions substantially the same as the test cell 10 of FIG. 1.

Figure 3:
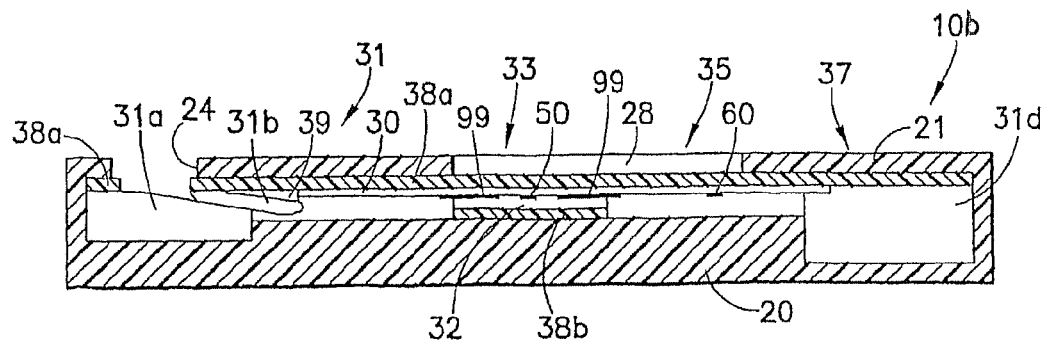
FIG. 3 is a cross-sectional view of a third embodiment of the invention.

Turning now to FIG. 3, a third embodiment of the invention is seen. In FIGS. 1, 1A, 1B and 3, like numbers are used for like elements. Thus, it will be appreciated that the primary difference between test cell 10b of the third embodiment of FIG. 3 and test cell 10 of the first embodiment of FIGS. 1, 1A, and 1B is that overlying the second nitrocellulose strip 32 at the location where the first nitrocellulose strip 30 contacts the second strip (except for a narrow zone at and adjacent test site 50) is a very thin layer of non-porous material 99 such as plastic. As a result of material 99, the strips 30 and 32 contact each other almost exclusively at the location of the test line 50. Those skilled in the art will appreciate that the immunoassay test cell 10b of FIG. 3 may be used in the same manner and functions substantially the same as the test cell 10 of FIG. 1.

Figure 4:
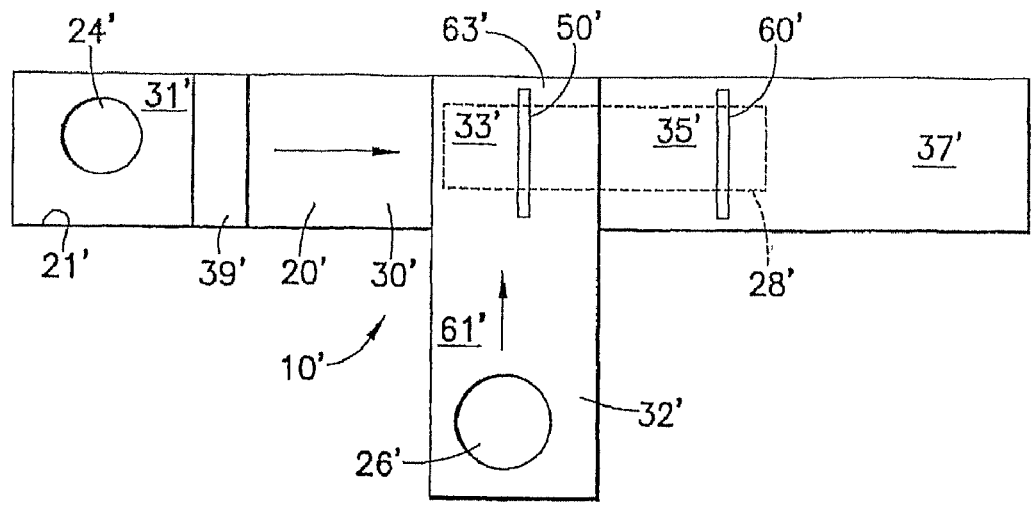
FIG. 4 is a top schematic view of a fourth embodiment of the invention.

Turning now to FIG. 4, a fourth embodiment of the immunoassay device is shown with a test cell 10' (slightly modified relative to test cell 10 of FIG. 1) provided which includes: a T-shaped housing 20' having a top wall 21' defining first and second holes 24', 26', and a window 28'; and first and second sorbent or bibulous materials 30', 32' defining perpendicular horizontal flow paths in the housing. The first sorbent material 30' includes at least two and preferably three or four zones and may be made from a plurality of materials. A first zone 31' (sometimes called a filter zone) is located at the first hole 24' and extends to a second zone 33' (sometimes called a test zone) which is located at the junction of the "T". The first zone 31' preferably includes a filter, a pad on or in which a conjugate 39' having desired antigens or antibodies with attached colored markers is deposited and immobilized, and a thin membrane typically made from nitrocellulose (which extends to the second and optional third and fourth zones) with a backing. The first zone 31' is adapted to receive a buffer solution, to cause the buffer solution to contact the conjugate, thereby mobilizing the conjugate, and to wick the conjugate-carrying buffer solution to the second zone 33'. The second zone 33' has printed thereon a test line 50' which, as discussed hereinafter is located under the second sorbent material 32'. An optional third zone 35' (sometimes called a control zone) may be provided with a control line 60' typically containing antibodies to the conjugate antigens (or in some cases antibodies which will bind to conjugate antibodies, or even antigens which will bind to conjugate antibodies) as is well known in the art. Where the third zone 35' is provided, window 28' extends above the control line 60'. If desired, an optional fourth zone 37' (sometimes called a reservoir zone) may be provided as a wicking reservoir as is also well known in the art. The fourth zone 37' includes a relatively thicker absorbent paper. Preferably underlying all four zones is a thin plastic film having an adhesive which keeps the sorbent materials in place.

The second sorbent material 32' may also be made from a plurality of materials and preferably includes two zones 61', 63'. The first zone 61' (sometimes called a filter zone) is located at the second hole 26' and extends to the second zone 63' which is in contact with the second zone 33' of the first sorbent material 30'. If desired, the second zone 63' of the second sorbent material 32' may be printed with the test line 50' having immobilized antigens or antibodies (depending on whether the test cell is designed to test for the presence of antibodies or antigens) as is well known in the art. Regardless of whether second zone 63' or second zone 33' or both are provided with the test line 50', the test line 50' may be seen through the window 28' of clear plastic provided in the housing. As is suggested by the lines in FIG. 4 (compare FIG. 1), the second sorbent material 32' overlies the first sorbent material 30', such that the thin membranes of both materials are in contact with each other at least at the test line location. The second sorbent material 32' may be shaped as in FIG. 1 so that a standard nitrocellulose strip with backing is provided. Alternatively, material 32' may be shaped as in FIG. 2 such that it touches the first sorbent material almost exclusively at the location of the test line 50'. As another alternative, the material 32' may be shaped as in FIG. 1, and a thin non-porous membrane can be provided as in FIG. 3 such that materials 30' and 32' touch each other almost exclusively at the location of the test line 50'.

Those skilled in the art will appreciate that the immunoassay test cell 10' of FIG. 4 may be used in the same manner and functions substantially the same as the test cell 10 of FIG. 1.

Figure 5:
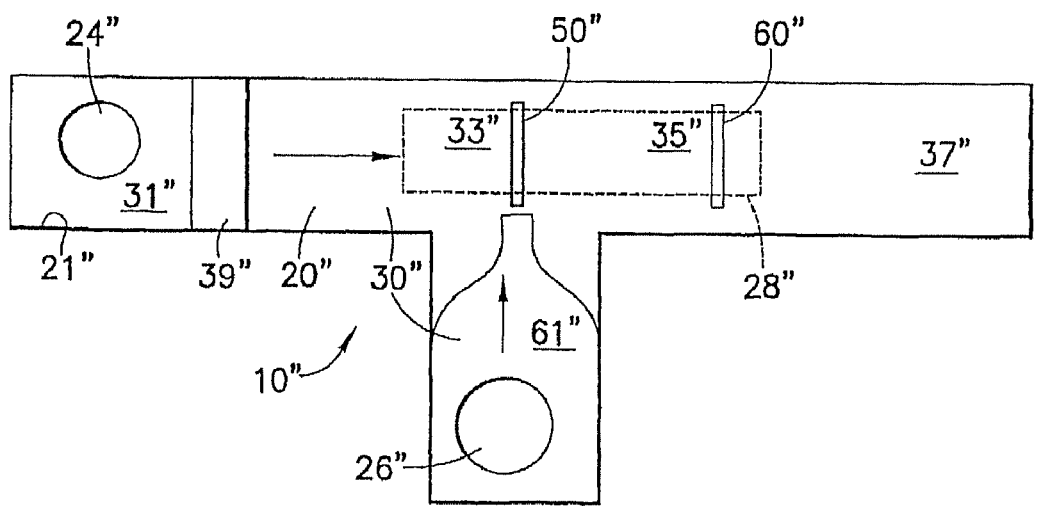
FIG. 5 is a top schematic view of a fifth embodiment of the invention.

Turning now to FIG. 5, an immunoassay device test cell 10" is provided and includes: a T-shaped housing 20" having a top wall 21" defining first and second holes 24", 26", and a window 28"; and a T-shaped sorbent or bibulous material 30" defining perpendicular flow paths in the housing. The T-shaped sorbent material 30" includes at least three and preferably four or five zones and may be made from a plurality of materials. A first zone 31" (sometimes called a filter zone) is located at the first hole 24" and extends to a second zone 33" (sometimes called a test zone) which is located at the junction of the "T". The first zone 31" preferably includes a filter, a pad on or in which a conjugate 39" having desired antigens or antibodies with attached colored markers is deposited and immobilized, and a thin membrane typically made from nitrocellulose and a backing therefor. The first zone 31" is adapted to receive a buffer solution, to cause the buffer solution to contact the conjugate, thereby mobilizing the conjugate, and to wick the conjugate-carrying buffer solution to the second zone 33". The second (test) zone 33" is preferably printed with a test line 50" having immobilized antigens or antibodies (depending on whether the test cell is designed to test for the presence of antibodies or antigens) on the membrane as is well known in the art. The test line 50" may be seen through the window 28" of clear plastic provided in the housing. The third zone 61" (sometimes also called a filter zone) is located at the second-hole 26", is perpendicular to the strip defined by the first and second zones, and extends to the second zone 33". An optional fourth zone 35" (sometimes called a control zone) may also be printed with a control line 60" typically containing antibodies to the conjugate antigens (or in some cases antibodies which will bind to conjugate antibodies, or even antigens which will bind to conjugate antibodies) as is well known in the art. Where the fourth zone 35" is provided, window 28" extends above the control line 60". If desired, an optional fifth zone 37" (sometimes called a reservoir zone) may be provided as a wicking reservoir as is also well known in the art. The fifth zone 37" includes a relatively thicker absorbent paper. Preferably underlying all of the zones is a thin plastic film having an adhesive which keeps the sorbent materials in place.

The embodiment of FIG. 5 differs from the embodiments of FIGS. 1-4 only in that instead of using two separate strips of material which overlie each other at the test zone, a single T-shaped membrane is utilized which defines a first horizontal strip with zones 31", 33" and preferably 35" and 37", and a second (integral) strip with zone 61" which touches the first strip at test zone 33". While the embodiment of FIG. 5 does not permit the horizontal flow paths to be tailored with materials of different pore sizes, two distinct migration paths are maintained as the first and third zones are not in fluid communication with each other except via the second (test) zone.

Figure 6:
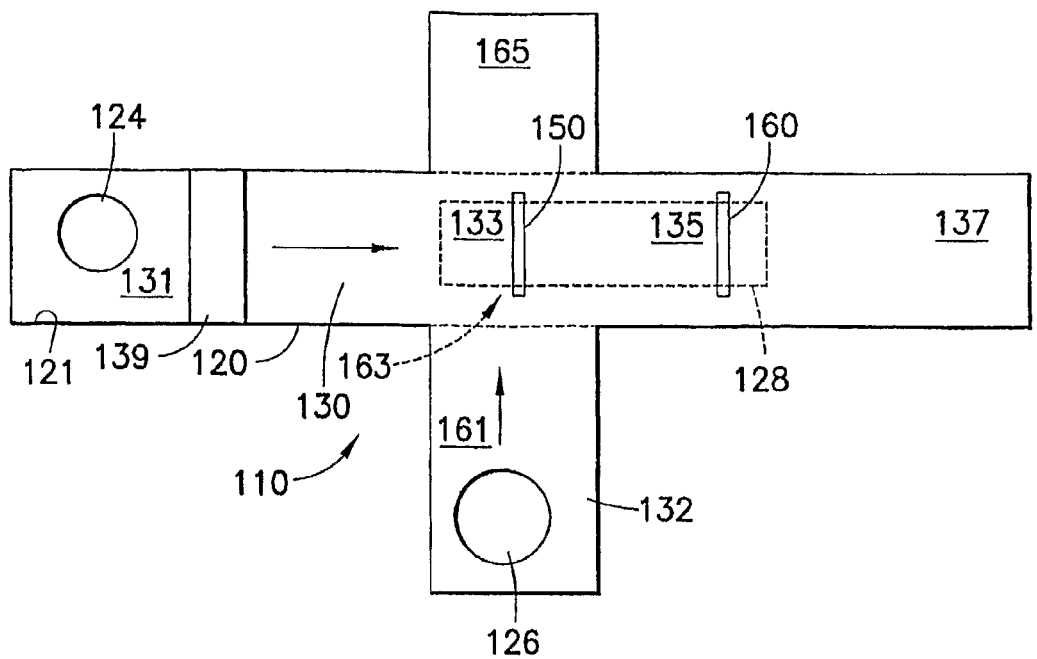
FIG. 6 is a top schematic view of a sixth embodiment of the invention.

Turning now to FIG. 6, an immunoassay device test cell 110 is provided and includes: a +-shaped housing 120 having a top wall 121 defining first and second holes 124, 126, and a window 128; and first and second sorbent or bibulous materials 130, 132 defining perpendicular flow paths in the housing. The first sorbent material 130 includes at least two and preferably three or four zones and may be made from a plurality of materials. A first zone 131 (sometimes called a filter zone) is located at the first hole 124 and extends to a second zone 133 (sometimes called a test zone) which is located at the junction of the "+". The first zone 131 preferably includes a filter, a pad on or in which a conjugate 139 having desired antigens or antibodies with attached colored markers is deposited and immobilized, and a thin membrane typically made from nitrocellulose. The first zone 131 is adapted to receive a buffer solution, to cause the buffer solution to contact the conjugate, thereby mobilizing the conjugate, and to wick the conjugate-carrying buffer solution to the second zone 133. The second (test) zone 133 is preferably printed with a test line 150 having immobilized antigens or antibodies (depending on whether the test cell is designed to test for the presence of antibodies or antigens) on the membrane as is well known in the art. The test line 150 may be seen through the window 128 of clear plastic provided in the housing. An optional third zone 135 (sometimes called a control zone) may also be printed with a control line 160 typically containing antibodies to the conjugate antigens (or in some cases antibodies which will bind to conjugate antibodies, or even antigens which will bind to conjugate antibodies) as is well known in the art. Where the third zone 135 is provided, window 128 extends above the control line 160. If desired, an optional fourth zone 137 (sometimes called a reservoir zone) may be provided as a wicking reservoir as is also well known in the art. The fourth zone 137 includes a relatively thicker absorbent paper. Preferably overlying the zones (in a manner such as seen in FIG. 1A) is a thin plastic film having an adhesive which keeps the sorbent materials in place.

The second sorbent material 132 may also be made from a plurality of materials and preferably includes at least three zones 161, 163, 165. The first zone 161 (sometimes called a filter zone) is located at the second hole 126 and extends to the second zone 163 which is in contact with the second zone 133 of the first sorbent material 130. If desired, the sorbent material 132 may be printed with the test line 150 at the second zone 163 instead of or in addition to second zone 133 of material 130. As is suggested by the dotted lines in FIG. 6, the first sorbent material 130 overlies the second sorbent material 132 (as in the embodiment of FIG. 1). Alternatively, the second sorbent material 132 can be made to overlie the first sorbent material 130 (as in the embodiment of FIG. 4), in which case the adhesive films where utilized, and other elements should be properly arranged. If desired, an optional third zone 165 (sometimes called a reservoir zone) may be provided as a wicking reservoir. The fourth zone 137 includes a relatively thicker absorbent paper. If desired, a thin plastic film having an adhesive which keeps the second sorbent material in place may be utilized.

Figure 7:
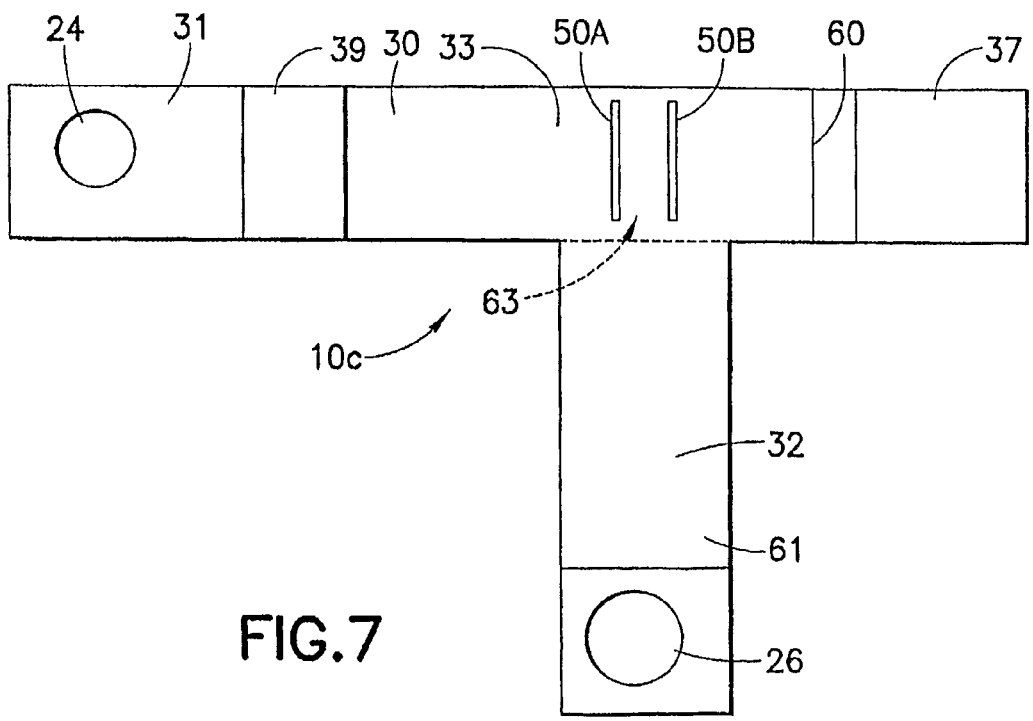
FIG. 7 is a top schematic view of a seventh embodiment of the invention.

In FIG. 7, a seventh embodiment of the invention is seen. In FIGS. 1, 1A, 1B and 7, like numbers are used for like elements. Thus, it will be appreciated that the primary difference between the seventh embodiment of FIG. 7 and the first embodiment of FIGS. 1, 1A, and 1B is that two test lines 50A and 50B are printed on zone 33 of first sorbent material 30 and/or on zone 63 of second sorbent material 32. The two test lines 50A and 50B preferably include different immobilized antigens or antibodies. For example, one of the lines (e.g., line 50A) could include HIV1 peptides and/or recombinant antigens such as gp41/gp120, while the other line (e.g., line 50B)

could include HIV2 peptides and/or recombinant antigens such as gp36. As another example, one of the lines could include HIV1, HIV2, or HIV1/2 peptides and/or recombinant antigens, while the other line includes tuberculosis antigens. As discussed below, where the test lines include immobilized antibodies or antigens that will not bind to a single conjugate (such as Protein A), it may be desirable to use a plurality of different conjugates having desired antigens or antibodies with attached colored markers. Those skilled in the art will appreciate that the immunoassay test cell 10c of FIG. 7 may be used in the same manner and functions substantially the same as the test cell 10 of FIG. 1, except that a "positive" test indicating the presence of a first antibody (or antigen) being tested in the sample is obtained when test line 50A and the control site 60 show lines of color; a "positive" test indicating the presence of a second antibody (or antigen) being tested in the sample is obtained when test line SOB and the control site 60 show lines of color; and a "positive" test indicating the presence of both the first and second antibodies (or antigens) being tested in the sample is obtained when test lines 50A and 50B and the control site 60 show lines of color. A "negative" test indicating the lack of the presence of the antibody (or antigen) in the sample is obtained when only the control site 60 (and neither of test lines 50A and 50B) shows a line of color. An invalid test is obtained when the control site does not show a line of color.

Figure 8:
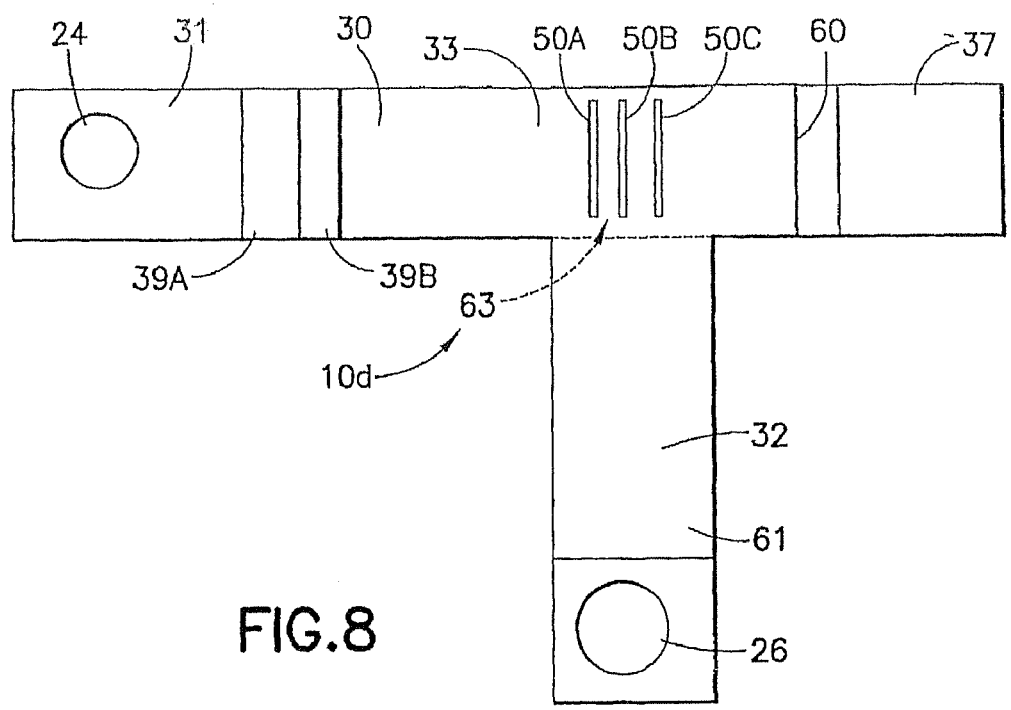
FIG. 8 is a top schematic view of an eighth embodiment of the invention.

In FIG. 8, an eighth embodiment of the invention is seen. In FIGS. 1, 1A, 1B and 8, like numbers are used for like elements. Thus, it will be appreciated that the primary differences between the eighth embodiment of FIG. 8 and the first embodiment of FIGS. 1, 1A, and 1B is that three test lines 50A, 50B, 50C are printed on zone 33 of first sorbent material 30 and/or on zone 63 of second sorbent material 32, and that two different latex conjugates 39A, 39B are utilized. The three test lines 50A, 50B, and 50C preferably include different immobilized antigens or antibodies. For example, one of the lines (e.g., line 50A) could include p24 monoclonal antibodies, a second line (e.g., line 50B) could include HIV1 peptides and/or recombinant antigens such as gp41/gp120, while the third line (e.g., line 50C) could include HIV2 peptides and/or recombinant antigens such as gp36. In this case, two conjugates 39A, 39B are provided, with conjugate 39A being a latex conjugate with protein A which will bind to HIV1 and HIV2 antibodies, if present, but will not bind to the p24 antigen, and conjugate 39B being a latex conjugated to p24 monoclonal which will bind to the p24 antigen in the sample, if present, but will not bind to the HIV1 and HIV2 peptides and/or recombinant antigens. As shown in FIG. 8, the conjugates 39A and 39B are located at different locations of the migration path (e.g., on two portions of a single pad, or on two connected pads). However, it will be appreciated that the conjugates 39A and 39B may be applied to the same location as a mixture. Those skilled in the art will appreciate that the immunoassay test cell 10d of FIG. 8 may be used in the same manner and functions substantially the same as the test cell 10 of FIG. 1, except that a "positive" test for HIV is indicated by the visibility of color at one or more of lines 50A, 50B, 50C, and at control line 60, a "negative" test is indicated by the visibility of color at control line 60 only, and an "invalid" test is indicated when no color appears at control line 60.

Figure 9:
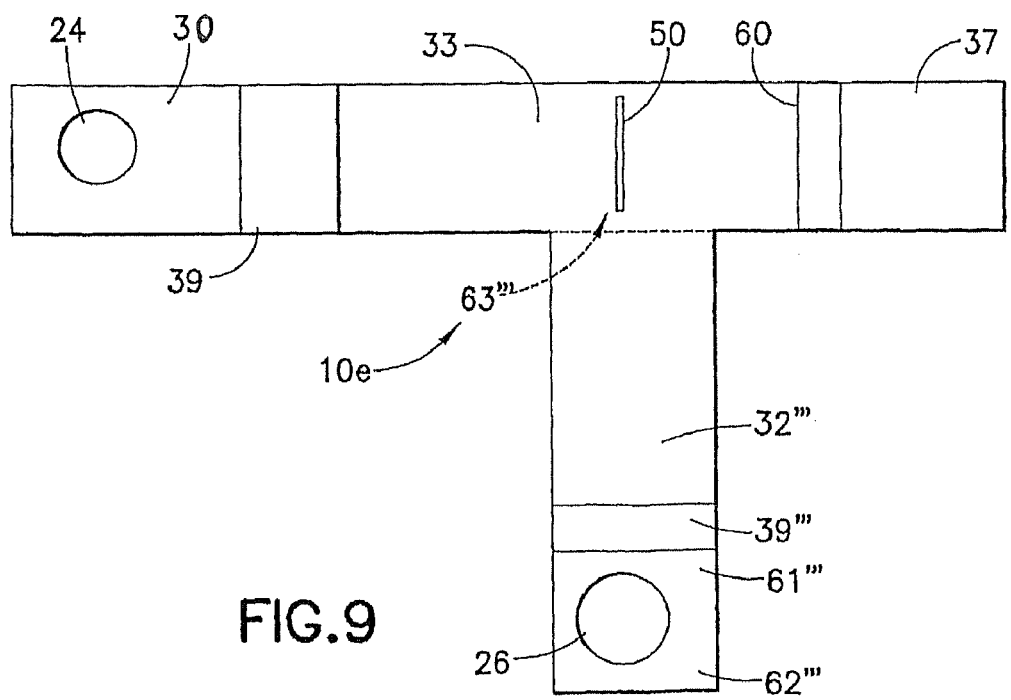
FIG. 9 is a top schematic view of a ninth embodiment of the invention.

A ninth embodiment of the invention is seen in FIG. 9. In FIGS. 1, 1A, 1B and 9, like numbers are used for like elements. Thus, it will be appreciated that the primary difference between the ninth embodiment of FIG. 9 and the first embodiment of FIGS. 1, 1A, and 1B is that the second sorbent material 32''' includes a first zone 61''' (sometimes called a filter zone) having a filter or pad 62''' which has thereon a conjugate 39''' of an antibody bound to an interim binding agent (without marker), and the test zone has a test line 50 of an immobilized binding agent. The interim binding agent and immobilized binding agent are chosen for their ability to selectively bind extremely well to each other. Thus, for example, the interim binding agent may be biotin and the immobilized binding agent may be streptavidin. The conjugate 39''' in the sample migration path may therefore be an antibody such as a p24 monoclonal antibody which is bound to biotin. Likewise, the conjugate 39 in the buffer migration path is preferably a latex marker conjugate with an antibody (e.g., a monoclonal antibody) which will bind to the antigen of interest.

With the test cell 10e of FIG. 9 which is arranged to detect a p24 virus, a sample is first added to the second sorbent material 32'''. When the sample reaches the p24 monoclonal antibody—biotin conjugate 39''', the p24 antigen (virus), if present in the sample, will bind with the p24 monoclonal antibody—biotin conjugate, and will migrate to the test area 63''' of strip 32''' where the biotin will be captured by the streptavidin at the test line 50 located on strip 32''' and/or on strip 30. Thus, the test line 50 will have a complex of streptavidin bound to biotin which is bound to a p24 monoclonal antibody which in turn is bound to a p24 antigen. Buffer is then added to the first sorbent material 30. The buffer carries the latex marker—monoclonal antibody conjugate 39 to the test area 33 where the monoclonal antibody of the conjugate 39 binds to the p24 antigen held at the already present complex, thereby presenting a colored line due to the marker. If no antigen is present in the sample, the biotin—p24 monoclonal antibody conjugate 39''' will still bind to the streptavidin, leaving a complex of streptavidin, biotin, and p24 monoclonal antibody at the test line. However, when the latex marker monoclonal antibody conjugate 39 reaches the test area, the monoclonal antibody will have no antigen with which to bind. Thus, no marker conjugate 39 will be held at the test line 50, and a "negative" test will be registered.

It will be appreciated by those skilled in the art that the system of FIG. 9 provides a major advantage over traditional lateral flow systems of the art due to the high affinity of the interim binding agent (e.g., biotin) and the immobilized binding agent (e.g., streptavidin) which results in an extremely sensitive test.

Figure 10:
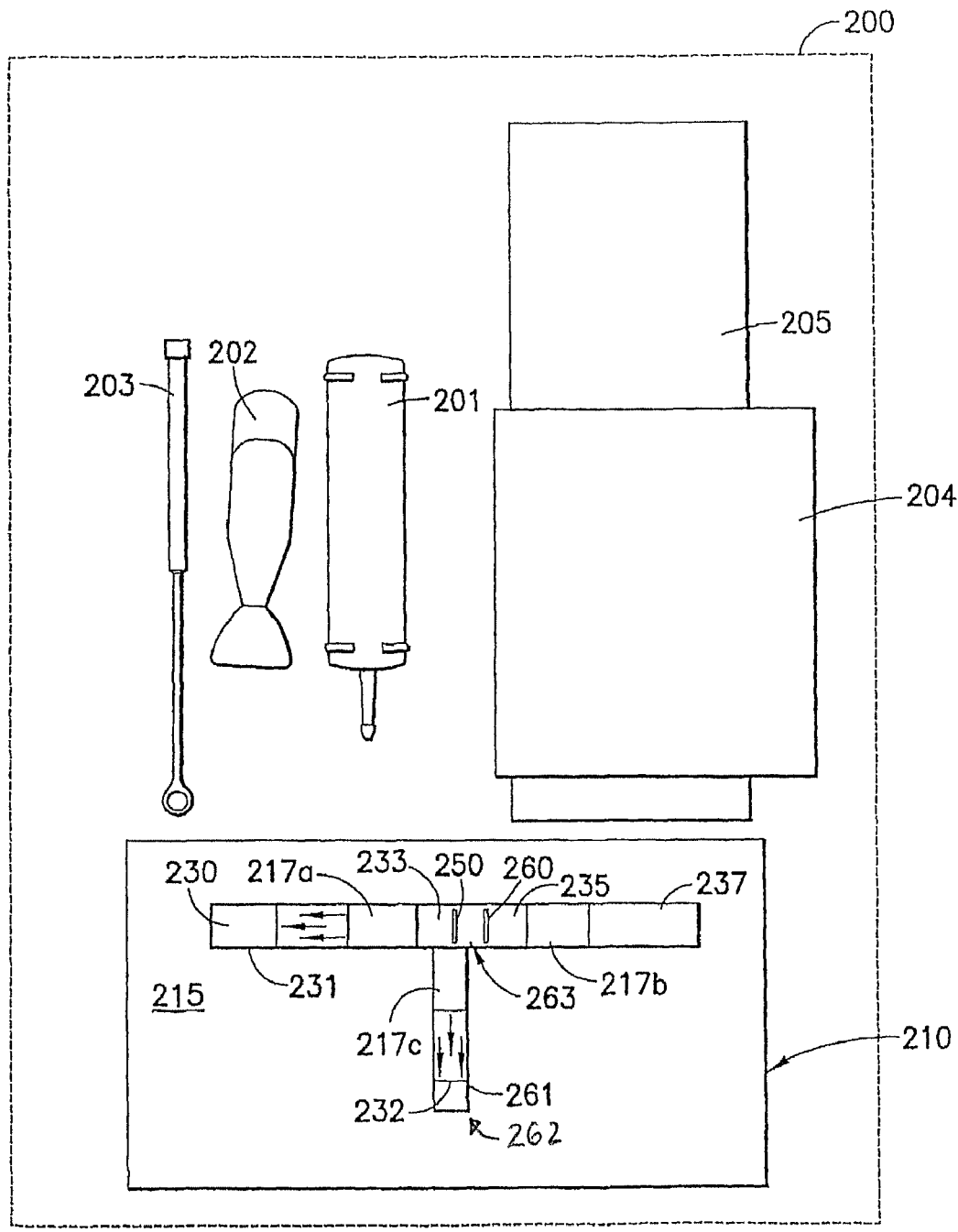
FIG. 10 is a top schematic view of an implementation of the invention which does not use a housing.

Turning now to FIG. 10, an immunoassay test kit 200 is provided and includes a lancet 201, a buffer pack 202, a loop 203, an alcohol wipe 204, an adhesive bandage 205, and a test device or test cell 210. The test cell 210 is similar to the test cells of the other embodiments, with certain exceptions such as a cardboard backing 215 which is provided instead of a housing, and paper covers 217a, 217b, 217c which are provided over various portions of the sorbent materials. Arrow indicia are preferably provided to indicate in which direction to pull paper covers 217a, 217b for removal from the sorbent materials. More particularly, test cell 210 includes first and second sorbent or bibulous materials 230, 232 defining perpendicular horizontal flow paths. The first sorbent material 230 includes at least two and preferably three or four zones and may be made from a plurality of materials. A first zone 231 (sometimes called a filter zone) is located at one end of the first sorbent material and extends to a second zone 233 (sometimes called a test zone) which is located at the junction of the "T". The first zone 231 preferably includes a filter, a pad on or in which a conjugate (not shown) having desired antigens or antibodies with attached colored markers is deposited and immobilized, and a first portion of a thin membrane or sorbent or bibulous material 230 typically made from nitrocellulose with a plastic backing (not shown). The first zone 231 is adapted to receive a buffer solution, to cause the buffer solution to contact the conjugate, thereby mobilizing the conjugate, and to wick the conjugate-carrying buffer solution to the second zone 233. At least a portion of the first zone is typically covered by a paper cover 217a. The second (test) zone 233 includes a second portion of the thin membrane 230 which is preferably printed with one or more test lines (one shown) 250 having immobilized antigens or antibodies (e.g., gp41/gp120 and gp36 peptides for the detection of HIV1/2) on the membrane as is well known in the art. The sorbent material at the test line 250 may be uncovered or covered by a clear plastic cover (not shown). An optional third zone 235 (sometimes called a control zone) which includes a third portion of the thin membrane 230 may also be printed with a control line 260 typically containing antibodies to the conjugate antigens (or in some cases antibodies which will bind to conjugate antibodies, or even antigens which will bind to conjugate antibodies) as is well known in the art. The third zone may likewise be left uncovered or covered by a clear plastic cover. If desired, an optional fourth zone 237 (sometimes called a reservoir zone) may be provided as a wicking reservoir as is also well known in the art. The fourth zone 237 includes a relatively thicker absorbent paper, and may be covered by cover 217b. Preferably underlying zones 231, 235, and 237 is a thin adhesive strip (not shown) which keeps the sorbent materials in place. The adhesive strip is laid down atop the cardboard 215.

The second sorbent material 232 may also be made from a plurality of materials and preferably includes two zones 261, 263. The first zone 261 (sometimes called a filter zone) includes a filter or pad 262 and a first portion of a thin membrane or sorbent or bibulous material 232 typically made from nitrocellulose with a backing (not shown). The first zone 261 extends to the second zone 263. At least a portion of the first zone is typically covered by a paper cover 217c. The second zone 263 includes a second portion of the thin membrane 232 which is in contact with the second zone 233 of the first sorbent material 230. The second sorbent material 232 underlies the first sorbent material 230 such that the membranes are in contact with each other and such that the test line 250 is effectively located between the membranes. Thus, test line 250 could be printed on the second zone 263 of the second sorbent material 232 instead of, or in addition to the second zone 233 of the first sorbent material 230. Preferably underlying zones 261 and 263 is a thin adhesive strip (not shown) which keeps the second sorbent material in place. The adhesive strip is laid down atop the cardboard 215.

It will be appreciated that the test device 210 of FIG. 10 can be modified to assume any of the configurations of the previously described embodiments.

A user uses the test kit of FIG. 10 by opening a blister pack (not shown) containing all of the kit elements, removing a paper cover (if provided) from the test device 210, opening the alcohol wipe package and wiping his/her finger with the alcohol wipe 204, taking the lancet 201 and pricking his/her wiped finger in order to draw blood. Then, preferably using the loop 203, the user gathers a drop of blood (e.g., 5 microliters) and places the drop of blood onto the non-covered portion of zone 261 of the second sorbent material 232. The user may then open the adhesive bandage package and place the adhesive bandage 205 over the pricked finger. The user then opens the buffer pack 202 and squeezes one drop (e.g., 30 microliters) of buffer onto the same location as the blood in zone 261. After waiting a desirable amount of time (e.g., 5 minutes) for the blood to migrate to the test zone 263, the user adds to two drops (e.g., 60 microliters) of buffer to the first zone 231 of the first sorbent material 230. After waiting a desirable amount of time (e.g., 7 minutes) after the buffer was added to zone 231, the test line 250 and control line 260 are viewed. A "positive" test is indicated by the appearance of color at both the test line 250 and the control line 260. A "negative" test is indicated by the appearance of color at the control line 260 and no color at the test line 250. If no color appears at the control line 260, the results of the test are invalid.

According to other embodiments of the invention, instead of providing a dry conjugate deposit having desired antigens or antibodies with attached colored markers in the test cell, the test cell does not include a dry conjugate at all. Rather, a (wet) buffer-conjugate subsystem is utilized, and the conjugate pad (31b-FIG. 1A) is not required such that the thin nitrocellulose strip or other sorbent material may be coupled directly to the filter (31a-FIG. 1A). Thus, after the sample has been deposited in the second hole in the housing and permitted to migrate to the test site, the buffer-conjugate subsystem is deposited in the first hole in the housing and likewise permitted to migrate to the test site.

According to further embodiments of the invention, instead of the viewing window being provided in the top of the housing, a window is provided in the bottom of the housing.

It will be appreciated by those skilled in the art that the embodiments of the invention may be realized using many different materials. For example, the sorbent material(s), which typically include a very thin, inert film, strip, sheet, or membrane may be formed from nitrocellulose, filter paper, silica, or from, e.g., microporous or microgranular woven or non-woven fabrics, or combinations thereof. Many types of suitable materials and combinations thereof are described in U.S. Pat. No. 4,960,691 to Gordon et al. and U.S. Pat. No. 4,956,275 to Zuk et al. which are both hereby incorporated by reference in their entireties. Often, the nitrocellulose or other sorbent materials will be provided with a thin non-porous inert plastic backing as previously described.

Thus, according to yet additional embodiments of the invention, the materials, thicknesses and lengths of the first and second sorbent materials are chosen to adjust the timing regarding the liquid sample and liquid buffer (or buffer-conjugate subsystem) reaching the test site. By providing separate migration paths for the sample/analyte and the buffer or buffer-conjugate subsystem, the materials may also be chosen to enhance sensitivity of the system.

In a similar vein, it will be appreciated that the sorbent material can be shaped in any of many manners and take any of many dimensions as is known in the art. Thus, in order to help expedite wicking, the sorbent material can be key-shaped with the strip having smaller width at the first hole which receives the buffer solution and at the test site and control site, and a wider width at a reservoir zone. Such an arrangement is shown in U.S. Pat. No. 5,989,921 to Charlton et al., which is hereby incorporated by reference in its entirety herein. In any event, generally, the test strip will be substantially greater in length than in width, and substantially greater in width than in thickness. Indeed, in at least certain embodiments of the present invention, the strip at the test zone should be paper-thin (e.g., 0.1 mm thick) and sufficiently translucent such that the test and control lines can easily be seen through the test strip.

Further, the housing and the sorbent material can be integrated in an open lateral flow platform where injection molded polymer is provided with micro-pillars which enable exact control over flow by varying the height, diameter, shape and/or distance between the pillars. Such a platform essentially uses the same material for the housing and the sorbent wicking material and is sold by Amic AB of Uppsala, Sweden. See, e.g., www.amic.se. Since the injection molded polymer may be generally transparent, the entire housing may be considered the "window" through which the test and control lines/sites may be viewed.

It will also be appreciated that depending upon the type of test being constructed (e.g., pregnancy, HIV, tuberculosis (TB), prion, urine-analysis/drug, cardiac markers, cancer markers, Chagas, Chlamydia, dental bacteria (SM/LC), influenza A, influenza B, adenovirus, rotavirus, strep A, other bacteria or viruses, etc., and even veterinary applications such as CPV, FIV, FeLV, and heartworm), the antibody (or antigen) of interest will be different, and therefore the antigen (or antibody) used in the test strip will need to be tailored accordingly. Likewise, the antigen or antibody of the conjugate will need to be tailored accordingly. In some cases (such as HIV), the identical antigen may be utilized in the test strip as in the conjugate, as the binding site of the HIV antibody will bind with the HIV antigen at the test site and still provide additional binding sites for binding to the antigen-conjugate, while in other cases, different antigens might be required. Similarly, it will be appreciated that depending upon the type of test being constructed, the control site, where provided, will need to be tailored accordingly. Thus, for example, in an HIV antibody detection test, where the ligand being identified in the test zone will be the HIV 1 and/or HIV2 antibodies, the antigen in the test zone can be a mixture of HIV1 (e.g., gp41/gp120) and HIV 2 (gp36) peptides and/or recombinant antigens. The conjugate can be a colored latex or colloidal gold conjugated to protein A, Protein A/G, anti-human IgG/IgM, peptides or recombinant antigens.

It will also be appreciated by those skilled in the art that the marker of the conjugate may take many forms including different types of metal sols, a colored latex, any of various enzymes, etc. While the preferred embodiment of the invention provides a detection signal readily visible to the unaided eye, it will be appreciated that the invention encompasses other markers which can be detectible by ultraviolet radiation or other techniques such a fluoroscopy. Thus, it will be appreciated that a system employing the test cells of the invention which are read by an automatic reader such as a fluoroscopic or digital reader can be provided.

The present invention provides improved sensitivity without comprising the specificity of the assay. The main reasons for the sensitivity improvement are an improved migration of the sample to the test zone due to the distinct migration path, and the effective binding of the analyte to the binding site in the test zone prior to the reaction of the conjugated marker with the test zone complex. For example, in the case of an HIV test, HIV specific antibodies in the blood serum samples applied to the second sorbent strip will migrate to the test zone and will bind to the HIV test line(s). No other immunoglobulin G (IgG) in the blood will bind to the HIV antigens immobilized in the test zone. When buffer solution is added to the first sorbent strip to cause the protein A conjugate with latex or gold to migrate to the test zone, the protein A conjugate will bind to the FC part of the HIV antibodies which are already captured by the HIV peptides at the test line. Because the binding between protein A and the FC part of the HIV antibodies is very strong, only a small amount of HIV antibody needs to be present in order to be detected. This is in contrast to the traditional lateral flow HIV test systems where all human IgG (including HIV antibodies) in the blood sample will bind to the protein A before migration to the test line, because protein A binds non-specifically all IgG. Thus, the entire protein A, IgG, gold/latex complex will migrate to the test line which contains the HIV antigens. Only the HIV antibodies, protein A, gold/latex conjugates will then bind to the HIV antigens. However, because of the large amount of non-related IgG in the samples and the small amount of HIV antibodies present, there is a risk that not enough HIV antibodies will bind to the protein A, and the colored line will not be visible.

The increased sensitivity of the invention was tested by comparing TB immunoassays of the invention ("New Generation") substantially as shown in FIG. 10 against standard fast test TB immunoassays (TB Stat-Pak II). Sixteen samples were generated, with two samples at each of eight different levels of antibody (32 U/ml, 8 U/ml, 2 U/ml, 1 U/ml, ½ U/ml, ¼ U/ml, ⅛ U/ml, and a control of 0 U/ml. The results of the comparison testing is seen in FIG. 11, with the immunoassays of the invention showing at least an eight-fold increase in sensitivity relative to the standard prior art tests (i.e., a positive result being detected at ¼ U/ml for the immunoassay of the invention, and a questionable result being detected at 2 U/ml for the immunoassay of the prior art). In addition, twenty test of negative samples showed no false-positive results.

The increased sensitivity of the invention was also tested by comparing HIV1 and HIV2 immunoassays of the invention ("NG HIV test") substantially as shown in FIG. 10 against standard type fast test HIV immunoassays (HIV Stat-Pak). Samples were generated with different levels of dilution (1:64, 1:128, 1:256, 1:512, 1:1024, 1:2048, 1:4096; 1:8192 for HIV-1, and 1:4, 1:8, 1:16, 1:32, 1:64, 1:128, 1:256, 1:512, 1:1024, 1:2048 for HIV-2). The results of the comparison testing is seen in FIG. 12, with the immunoassays of the invention indicating an approximately four-fold increase in sensitivity relative to the standard prior art tests (i.e., the most sensitive positive result being detected for HIV1 at the 1:4096 dilution for the immunoassay of the invention, and the most sensitive positive result being detected at a 1:1024 dilution for the immunoassay of the prior art; and the most sensitive positive result being detected for HIV2 at the 1:512 dilution for the immunoassay of the invention, and the most sensitive positive result being detected at a 1:128 dilution for the immunoassay of the prior art). In addition, one hundred twenty tests of negative samples of the NG HIV tests showed a false-positive rate of less than 1 percent.

It is believed that the immunoassay test strip devices of the invention can provide decreased assay times relative to the devices of the prior art. In particular, it is known that blood, feces or saliva will migrate very slowly in the conventional chromatographic strip tests. However, in the immunoassay assay test strip devices of the invention, since a separate migration path is provided for the sample, the sorbent material utilized may be selected specifically relative to the test of interest in order to permit quick migration without concern relative to the conjugate migration, and therefore the assay time can be very fast relative to the prior art. For example, the first sorbent material 30, 30', 30", 130, 230 may be made of material having relatively small pores (by way of example and not limitation, less than 20 microns, and more preferably 3 to 15 microns), while the second sorbent material 32, 32', 32", 132, 232, may be made of material having relatively larger pores (by way of example and not limitation, more than 20 microns, and more preferably 25-40 microns). In this manner, the sample with the analyte will be able to more easily migrate down its path, while at the same time, a highly sensitive test strip line is provided in the relatively small-pored first sorbent material. In addition, as previously mentioned, by providing the second sorbent material with a pore size which is larger than the pore size of the first sorbent material, migration of the sample from the second sorbent material to the first sorbent material is desirably limited.

Examples of sorbent strips (membranes) having relatively smaller pores include MDI-08 (8 micron), MDI-10 (10 micron), MDI-15 (15 micron) from Advanced Microdevice of Ambala, India, and SP (3 micron), FP (5 micron) and RP (8 micron) from Whatman, Inc., of Floral Park, N.J. An example of a sorbent strip having relatively larger pores is P40 (30 micron) from Schleicher & Schuell Bioscience, Inc. of Keene, N.H.

Further yet, it is believed that the migration of conjugated particles in the absence of the sample provides a more uniform and consistent migration, resulting in an improvement of background clearance.

Another advantage of the immunoassay test strip devices of the invention is that they overcome aggregation/agglutination problems between the marker conjugate and analyte in the sample which is a major problem for large analytes (such as bacteria) in traditional chromatographic immunoassays. In the prior art, the large complex between bacteria and conjugated antibodies has difficulty in migrating to the test line. As a result, the complex tends to remain in the bottom of test strip or in the pad. With the present invention, the bacteria in the sample are applied (after filtering) directly to the test site, and immobilized there, while the marker conjugate is free to migrate without the sample to the test site. When the marker conjugate reaches the test site, bacteria already captured by the immobilized antibody in the test site will bind to the conjugate. Thus, the system of the present invention is extremely sensitive and specific.

Yet another advantage of the invention is the ability to provide tests for multiple infectious diseases with high sensitivity and without compromising specificity due to the cross-reactivity or decrease of sensitivity of multiple analytes when they have been printed as separate lines in a test zone. In particular, in traditional lateral flow assays, the sample and conjugate migrate together. If multiple test lines are provided in prior art devices, each line may retain analyte or cross-react with analyte so that the visible result at the following lines gets weaker and weaker. In contrast, with the present invention, samples containing several analytes will migrate to the test zone without the conjugate and will reach several lines at the same time. Thus, the analytes can bind equally to the several lines so that the same level of sensitivity can be maintained. Then, the conjugate is introduced in a distinct migration path and can bind to the complexes already immobilized at the lines. For example, for the simultaneous detection of HIV and TB antibodies in a patient sample, HIV antigens and TB antigens are immobilized as separate lines in the test zone, and the sample is provided to one strip for migration and for binding at the test zone. Buffer is then added to the other strip to permit the protein A gold or latex to migrate and bind to the HIV antigen-antibody complex and the TB antigen-antibody complex. Because of the high sensitivity of the test, TB will be detected if present. This is important, because in patients co-infected with HIV and TB, the antibody titer tends to be low for TB.

According to another aspect of the invention, where tests are provided for multiple infectious diseases (e.g., HIV and TB), different color latex particles can be used to conjugate to different antigens or antibodies provided in the conjugate pad or in the buffer solution. As a result, different color lines will appear at the test zone, with one color (e.g., red) corresponding to a first disease (e.g., HIV), and a second color (e.g., blue) corresponding to a second disease (e.g., TB).

As will be appreciated by those skilled in the art, the wait time between providing the sample to one sorbent strip, and providing buffer to the other sorbent strip can vary depending upon the viscosity of the sample and various attributes of the sorbent strip receiving the sample, including, e.g., pore size and strip length. Thus, typically, instructions will be included with the test device instructing the user to wait a predetermined amount of time (e.g., five minutes) after adding the sample (and optional buffer solution) to one strip, to add the buffer solution to the other strip. In order to obtain optimal results in the highest percentage of cases, the wait time is chosen to be substantially greater than what is actually needed. Thus, in accord with another aspect of the invention, in order to reduce wait time, visible food coloring or other water soluble dye is provided at the test site of any of the previously described embodiments of the invention. When the sample and optional buffer are provided to the test device, upon the sample migrating to the test site, the dye at the test site becomes diluted and disappears to the naked eye, thereby providing a visible indicator that the buffer may properly be added to the other strip without affecting the efficacy of the test.

With a test device provided with visible dye at the test site, the user is instructed to add the buffer solution after the color disappears at the test site. Thus, according to one method of the invention, a test device for determining the presence of a ligand in a liquid sample is provided with a test site having an immobilized ligand-binding mechanism and a visible soluble indicator. A sample is applied to the test device and the test site is viewed to observe the disappearance of the visible indicator. Thereafter, a solution (buffer) is applied to the test device. After some time, the test site may then be inspected to determine an indication of the presence or lack thereof of the ligand in the sample.

FIGS. 13A-13G are composite photograph/instructional diagrams of an HIV 1/2 test cassette product according to the invention which utilize a visible dye at the test site. The test product is constructed substantially according to any of the previously described embodiments and is provided with a plastic cassette housing with four openings or windows. A first of the four openings is marked S+B and is provided to receive a test sample plus buffer. A second of the four openings is marked B and is provided for receiving additional buffer. A third of the four openings is marked with numbers 1, 2, 3, 4, and 5 and is provided with test lines corresponding with five different HIV antigens or peptides (preferably p24, gp41, gp120, gp160, and gp36 respectively). A fourth opening marked C is provided with the control line. Test lines appearing in the third opening are provided with a color dye (e.g., blue) so that they are visible. The control line appearing in the fourth opening is also provided with a color dye (e.g., green) so that it is visible.

Figure 13C:
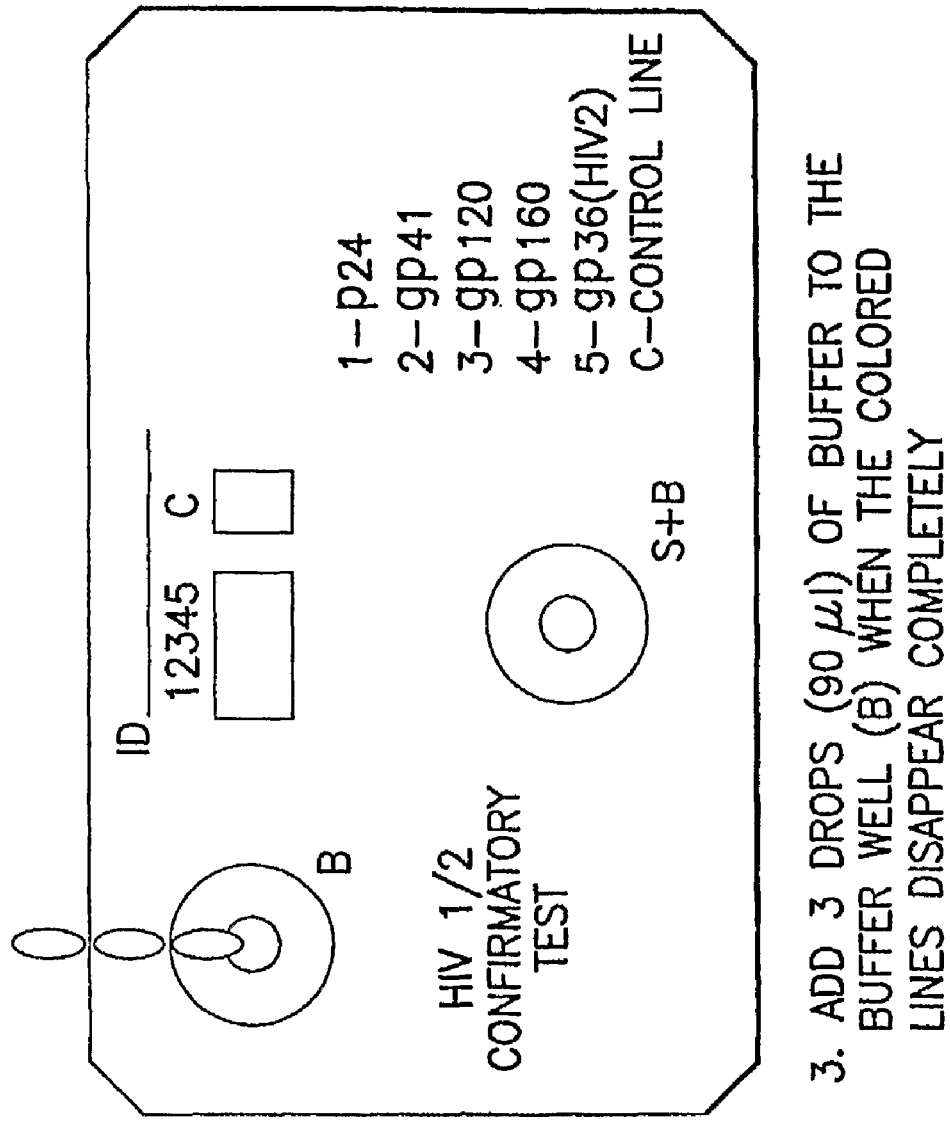
Figure 13G:
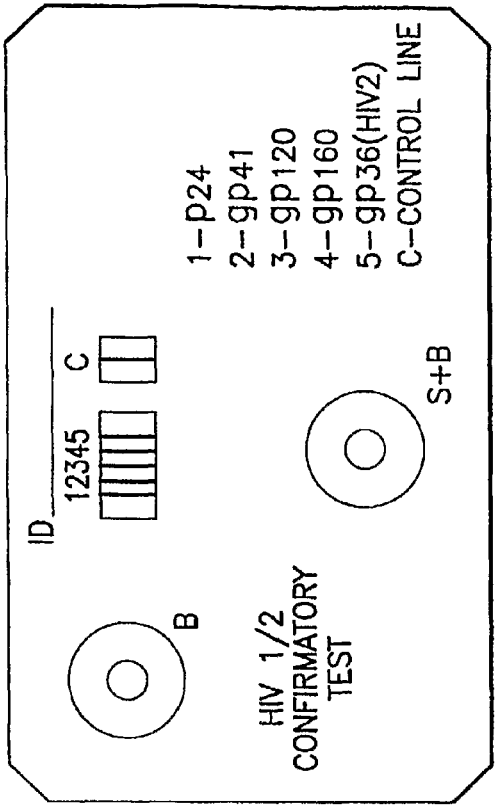
Figure 13F:
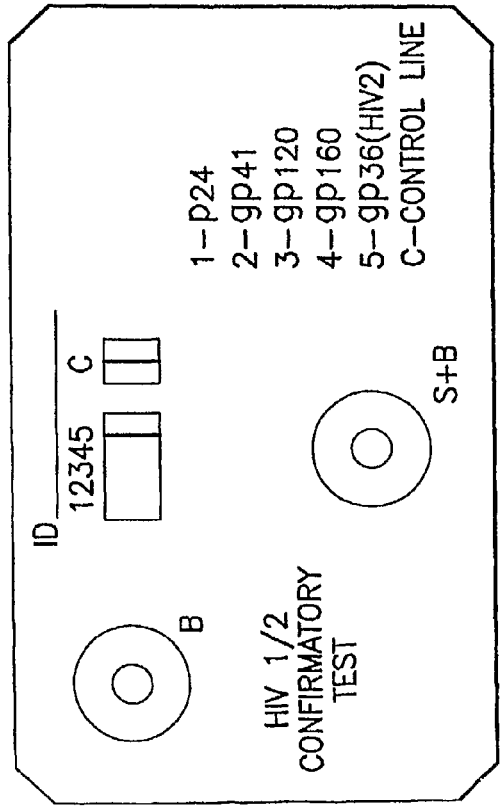
Figure 14C:
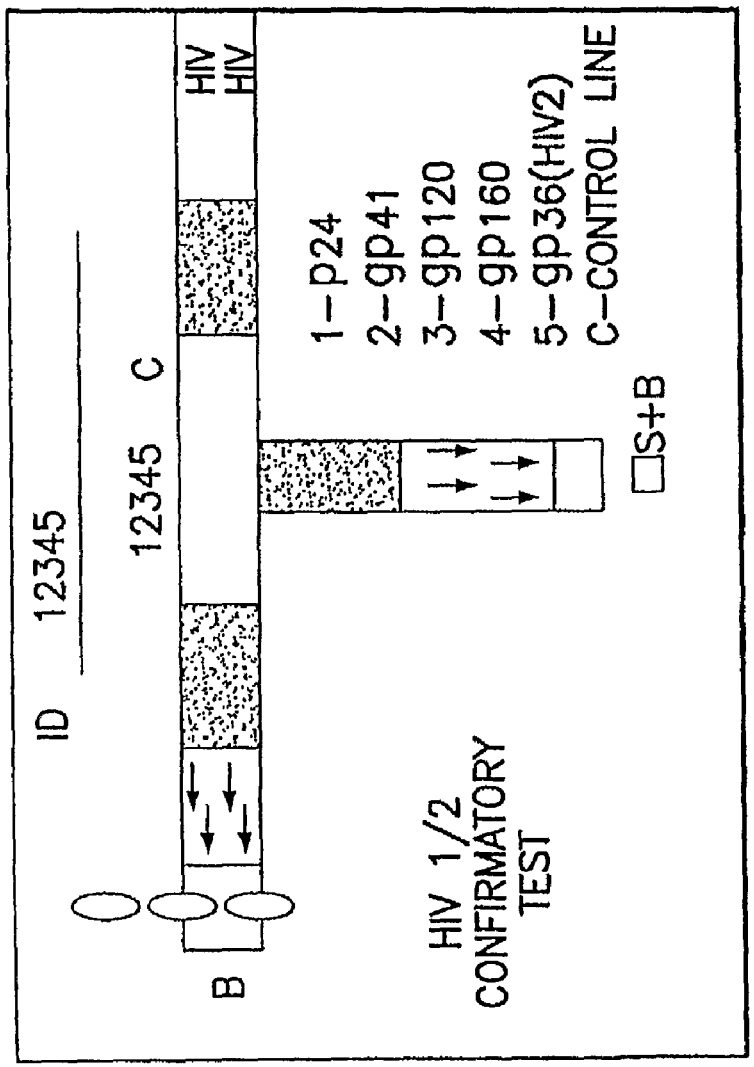
Figure 14D:
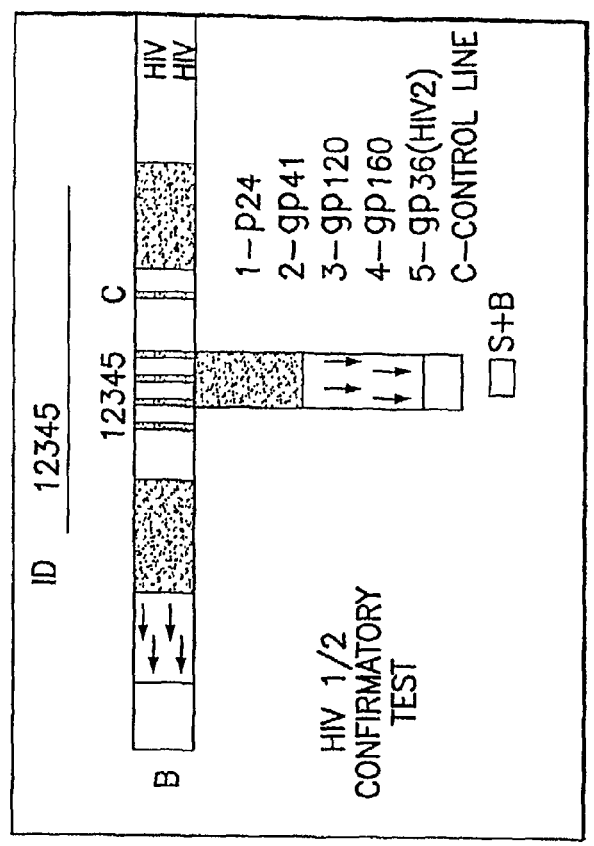
Figure 14E:
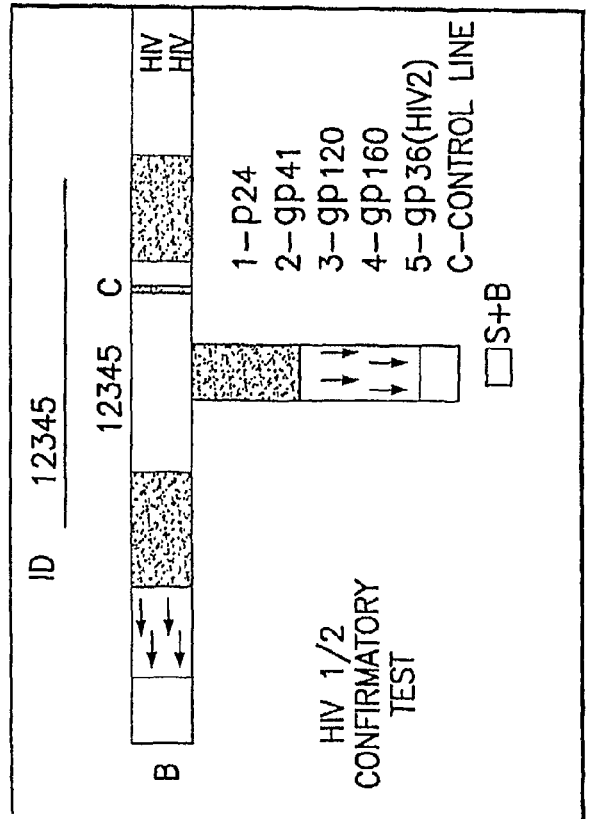
Figure 14F:
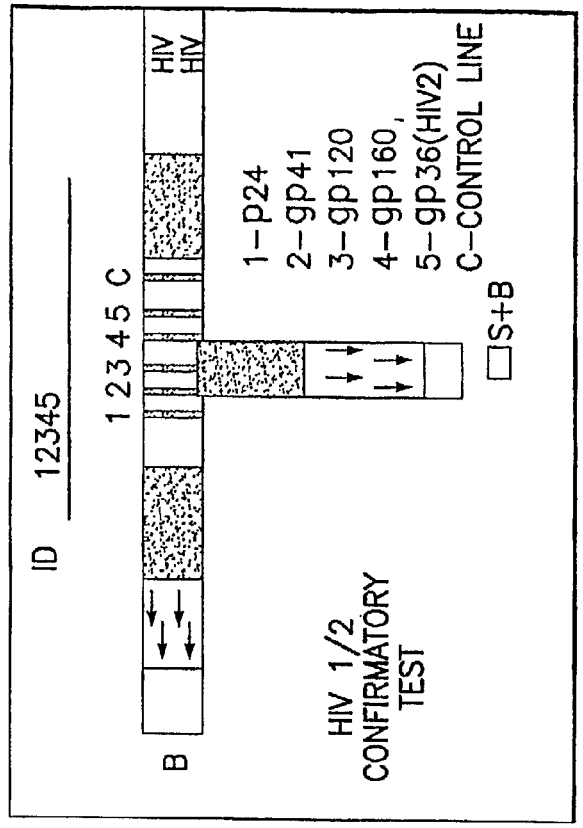
Figure 14G:
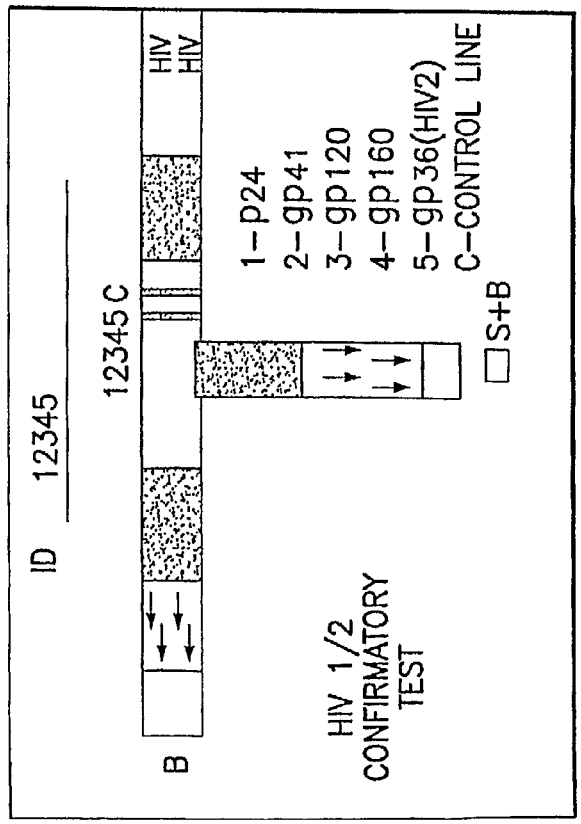
Figure 15C:
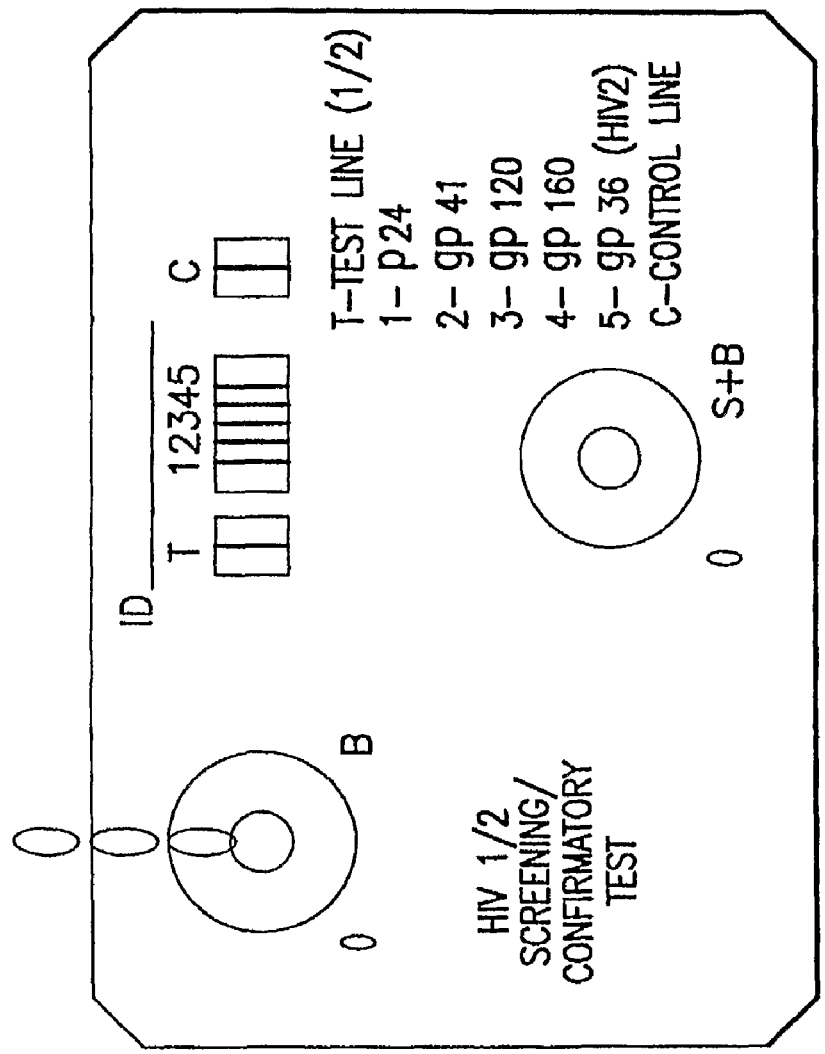
Figure 15D:
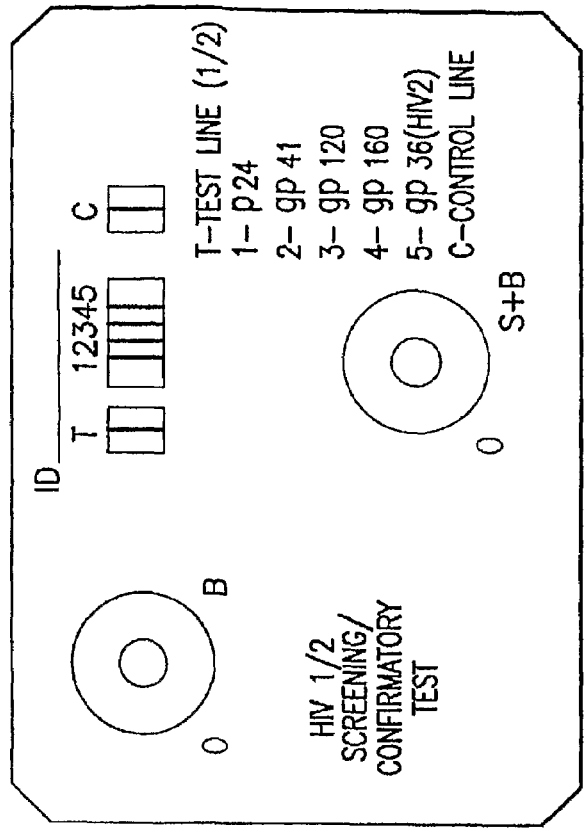
Figure 15E:
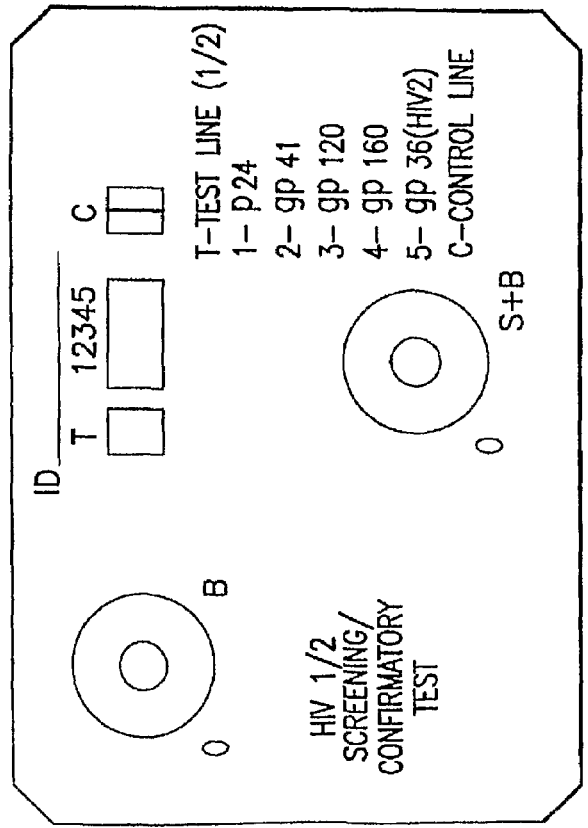
Figure 15G:
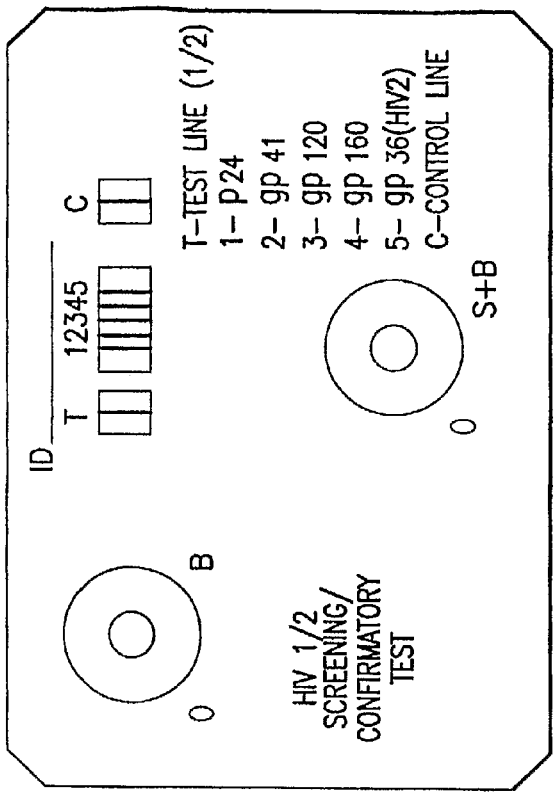
Figure 15F:
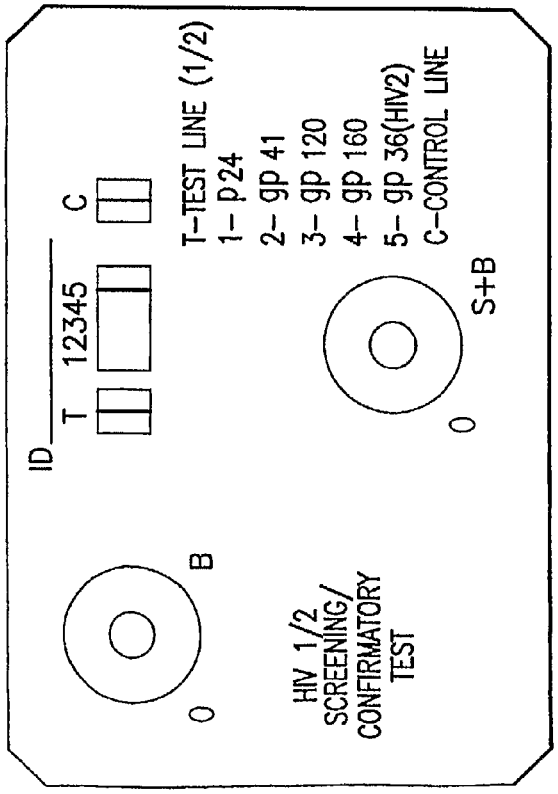

The apparatus shown in FIG. 13A is utilized by adding preferably approximately 10 µl of serum or blood to the sample well marked S+B. Then, as seen in FIG. 13B, preferably approximately 30 µl of buffer is added to the same sample well. Migration of the sample (typically with the help of the buffer) to the test zone will cause the dye at the test and control lines to dissipate. Disappearance of the dye from the lines confirms that the sample has reached the test area. At that time, and as shown in FIG. 13C, preferably approximately 90 µl of buffer is added to the opening marked B in order to cause migration of a conjugate marker to the test area. After a period of time, results may be read. Four examples of results are seen in FIGS. 13D-13G. In FIG. 13D, only the control line C is seen, thereby indicating a valid result that the sample tested negatively for HIV1 and HIV2 antibodies. In FIG. 13E, the control line and lines 1, 2, 3, and 4 are seen, thereby indicating a valid result that the sample tested positively for four different HIV1 type antibodies but negatively for HIV2 type antibodies. In FIG. 13F, the control line and line 5 are seen, thereby indicating a valid result that the sample tested positively for HIV2 type antibodies but negatively for the four different HIV1 type antibodies. In FIG. 13G, the control line and all lines 1-5 are seen, thereby indicating a valid result that the sample tested positively for four different HIV1 type antibodies and for HIV2 type antibodies. It is noted that if the control line C is not seen, the test results are not interpreted as being valid. It is also noted that it is possible that only one, two or three of lines 1-4 may indicate a positive result, as will be seen with reference to FIGS. 15A-15D, as a sample does not have to include all four different HIV1 type antibodies or none.

FIGS. 14A-14G are composite photograph/instructional diagrams of an HIV1/2 dipstick test product according to the invention. FIGS. 14A-14G correspond completely to FIGS. 13A-13G discussed above, except that instead of incorporating a plastic cassette with windows, the test product of FIGS. 14A-14G is a dipstick product on cardboard.

FIGS. 15A-15G are composite photograph/instructional diagrams of an HIV 1/2 confirmatory/test cassette product according to the invention which utilize a visible dye at the test site. The confirmatory/test product is substantially the same as the product of FIGS. 13A-13G and is constructed substantially according to any of the previously described embodiments, except that the product of FIGS. 15A-15G is provided with a plastic cassette housing with five openings or windows instead of the four of the product of FIGS. 13A-13G. A first of the five openings is marked S+B and is provided to receive a test sample plus buffer. A second of the five openings is marked B and is provided for receiving additional buffer. A third of the five openings is marked T and corresponds to a test line having all of the HIV antigens or peptides contained in the fourth window. The fourth of the five openings is marked with numbers 1, 2, 3, 4, and 5 and is provided with test lines corresponding with five different HIV antigens or peptides (preferably p24, gp41, gp120, gp160, and gp36 respectively). A fifth opening marked C is provided with the control line. Test lines appearing in the second and third openings are provided with a color dye (e.g., blue) so that they are visible. The control line appearing in the fourth opening is also provided with a color dye (e.g., green) so that it is visible.

The screening/confirmatory test product of FIGS. 15A-15G is utilized in the same manner as that of the product of FIGS. 13A-13G. The difference between the products is that the third window T provides a screening result which is digital; i.e., a yes or no answer to the sample containing HIV antibodies. In particular, because test line T contains a combination of all of the antigens or peptides provided on the test lines 1-5, it will be observable if any of the other test lines 1-5 is observed. The test lines 1-5 provide detail to the stated result; i.e., which HIV1 antibody or antibodies is/are detected, and whether an HIV2 antibody has been detected.

Figure 16B:
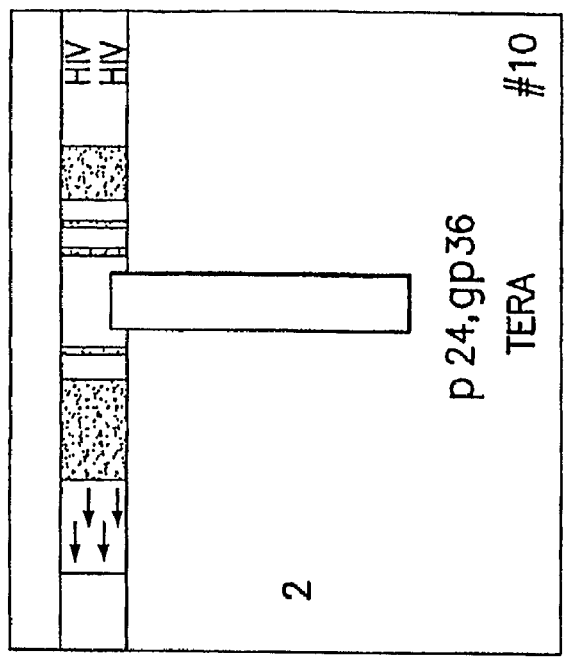
FIGS. 16A-16E are photographs of test results obtained on actual HIV 1/2 dipsticks of the invention.
Figure 16A:
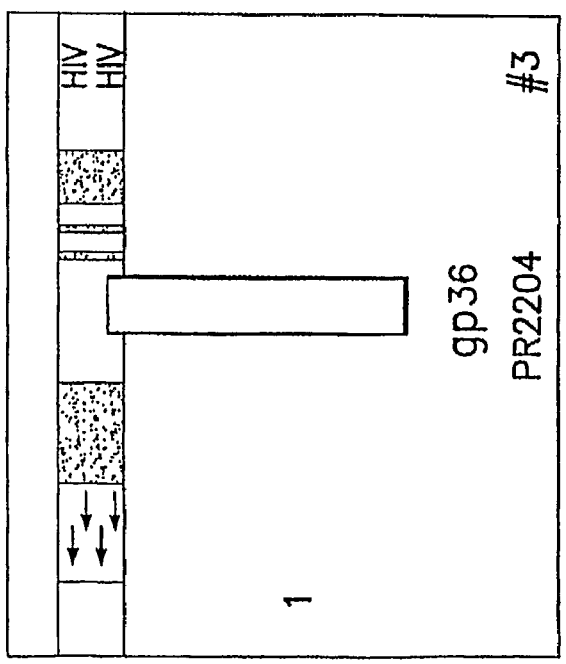
Figure 16C:
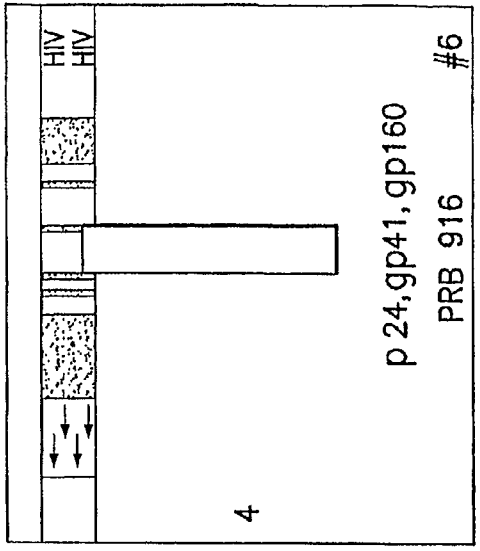
Figure 16D:
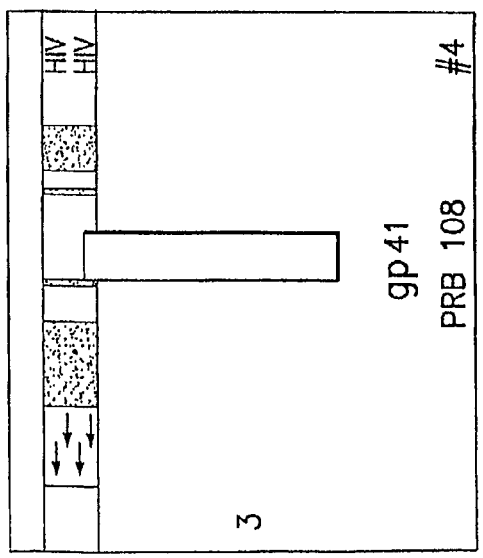
Figure 16E:
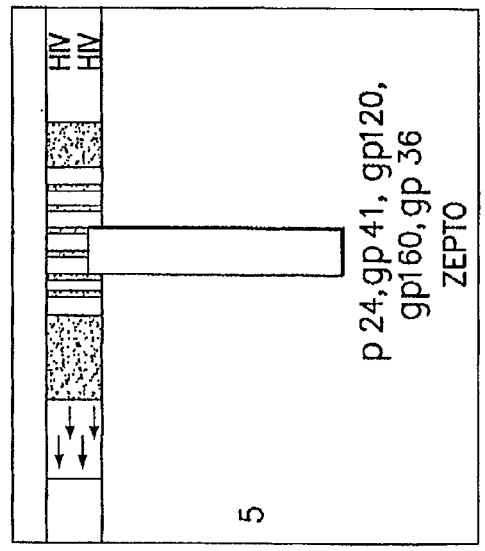

FIGS. 16A-16E are photographs of actual test results obtained on HIV 1/2 dipsticks of the invention. As seen in FIG. 16A, the control line and one line (gp36) are seen, indicating a valid test with the sample testing positive for HIV2 type antibodies. FIG. 16B shows observable control and first and fifth test lines, indicating a valid test with the sample testing positive for HIV1 antibodies which bind with the p24 antigen, and HIV2 type antibodies (which bind with the gp36 antigen), and negative for other HIV1 antibodies. FIG. 16C shows observable control and second test lines, indicating a valid test with the sample testing positive for HIV1 antibodies which bind with the gp41 antigen, and negative for other HIV1 antibodies and HIV2 type antibodies. FIG. 16D shows observable control and first, second, and fourth test lines, indicating a valid test with the sample testing positive for HIV1 antibodies which bind with the gp24, gp41 and gp160 antigens, and negative for other HIV1 antibodies and HIV2 type antibodies. FIG. 16E shows observable control and first through fifth test lines, indicating a valid test with the sample testing positive to all HIV1 antibodies and HIV2 antibodies being tested.

Example 1

HIV Test

Preparation of strip 1 for receiving sample and buffer—A test strip for the collection and transportation of the sample was prepared as follows. A nitrocellulose membrane (5×25 mm) of 20-30 micron pore size (Whatman Inc., USA) was laminated onto a plastic card. A sample pad of cellulose paper (S&S, Germany) was treated with PBS, 8.4 and NP40 and attached to the nitrocellulose membrane. The same procedure was used to make multiple test strips 1.

Preparation of strip 2 for receiving buffer only and with conjugate zone and test and control lines—A test strip for the detection of antibodies against HIV1 and HIV2 was prepared as follows. Synthetic HIV1 peptides gp41, gp120 and synthetic HIV2 peptide gp36 were biotinylated and then mixed with Avidin (Zymed, Inc. USA). This cocktail was filtered by a 0.2 micron filter and immobilized at a concentration of 0.25-0.50 mg/ml onto a nitrocellulose membrane of 10-15 micron pore size (MDI Ltd., Ambella, India) to be used as a test line using an ISO-Flow printer (Imagine Technology, Inc. USA). Protein A (Zymed Inc., USA) of concentration 0.25 mg/ml was immobilized in the same manner to be used as a control line. The membrane was dried for one hour at 37° C. The membrane was then laminated to a membrane backing (G&L, Inc. USA). A conjugate pad was prepared using a porous polyester matrix (Alstrom, Inc. USA). The pad was sprayed with protein A (Zymed Inc., USA) that was conjugated with purple colloidal gold particles of approximately 40 nm and OD 60 resuspended with conjugate buffer (50 mM PBS, sucrose, BSA, VPA, Tween 20) and dried at 37° C. for one hour. A test strip (7.2×62 mm) was prepared by attaching the gold conjugate pad, a sample pad (S&S Inc., Germany) and a sink pad (S&S Inc., Germany) to the nitrocellulose membrane attached to the laminate card. The same procedure was used to make multiple test strips 2.

Assembly of Strip 1 and Strip 2 in a cassette—Strip 2 (7.2×62 mm) was placed in the bottom part of the cassette with its laminate card on the bottom and the conjugate pad, sample pad, test and control lines facing up. Then, Strip 1 was placed in the bottom portion of the cassette. Strip 1 was placed so that it touched Strip 2 at the test site location with the nitrocellulose membrane of Strip 1 touching the nitrocellulose membrane of Strip 2. The top part of the cassette with separate openings for the sample and buffer, and with a window over the test and control site location was then placed onto the bottom portion of the cassette. The same procedure was used to make multiple assemblies (referred to below as Chembio DPP (dual path platform) HIV1/2 assemblies.

Test procedure—5 µl of serum/blood was added through the opening for the sample and 1 drop (40-50 µl) of buffer (PBS, pH 8.5-9.5, Chicken serum, EDTA, Tween 20) was immediately added to the through the same opening. After waiting one to two minutes until the sample reached the test zone and the color lines (quality control) disappeared, three or four drops (approximately 130-150 µl) of the same buffer were added through the opening for the buffer. After fifteen minutes, test results were read. The appearance of two pink lines (test and control) indicated a positive result. The appearance of a single band (control) indicated a negative result. The appearance of no bands would indicate an invalid result.

Test results—A commercial mixed HIV1 and HIV2 performance panel (PRZ-204) from BBI Inc., USA, was tested in assemblies prepared and assembled as above with the following results.

| PRZ-204 BBI | HIV Type | Chembio DPP HIV ½ | Western Blot 1 Cambridge Biotech | Western Blot 2 Genlabs | ELIA ½ Abbott |
|---|---|---|---|---|---|
| 1 | 1 | POS | POS | IND | POS |
| 2 | NEG | NEG | NEG | NEG | NEG |
| 3 | 2 | POS | IND | POS | POS |
| 4 | 2 | POS | POS | POS | POS |
| 5 | 1 | POS | POS | IND | POS |
| 6 | 2 | POS | IND | POS | POS |
| 7 | 1 | POS | POS | IND | POS |
| 8 | 2 | POS | IND | POS | POS |
| 9 | 1 | POS | POS | IND | POS |
| 10 | 1 | POS | POS | IND | POS |
| 11 | 2 | POS | POS | POS | POS |
| 12 | 2 | POS | POS | POS | POS |
| 13 | 1 | POS | POS | IND | POS |
| 14 | 1 | POS | POS | IND | POS |
| 15 | 2 | POS | IND | IND | POS |

All samples were correctly detected by the Chembio DPP HIV 1/2 and the ELIA 1/2 Abbott tests. Sample number 15 was indeterminate with both Wetern Blot tests as interpreted using ASTPHLD/CDC criteria (MMWR Vol. 38 S-7 1989), but were positive with the Chembio DPP HIV 1/2 and the ELIA 1/2 Abbott tests.

Example 2

Mycobacterium Tuberculosis (TB)

Test devices as in Example 1 were prepared for detection of antibodies against TB by modifying Strip 2 only. Strip 2 was modified by obtaining a mixture of TB recombinant antigens (F10, E6, P10, 14, 16) at a concentration of 1.0 mg/ml instead of the HIV peptides, and immobilizing the TB recombinant antigens at 0.5 µl/cm in a test line on the membrane to produce a first test line (T1). A second test line (T2) of TB antigen Lipoarabinmannan (LAM) at a concentration of 0.05 mg/ml and immobilized at 0.5 µl/cm was immobilized in the test area as well. Protein A diluted with PBS 7.4 concentration of 0.25 mg/ml was immobilized as the control line. Protein A/G (Pierce, USA) and anti-human IgM (Sigma, USA) conjugated with purple colloidal gold particles of approximately 40 nm were applied to the conjugate pad.

Test procedure—The test procedure for the TB test was the same as for Example 1 except that the sample volume was 10 µl of serum.

Test results—A total of 300 commercial TB samples (Zeptometrix Inc, USA) were evaluated with the DPP TB test. All positive samples had a culture positive result but some of the samples were smear negative and HIV co-infected. An overall sensitivity and specificity of 75% and 90% respectively was achieved with this endemic samples.

Example 3

HIV Confirmatory Dipstick

Test devices in the form of confirmatory test strips for the detection of HIV1 and HIV2 antibodies were prepared as in Example 1. However Strip 1 and Strip 2 were attached using an adhesive (G&L Inc, USA) on a laminate card without any plastic housing (i.e., a "dipstick"). Five different antigens HIV1 (p24, gp41, gp120, gp160) and HIV2 (gp36) were immobilized (0.25-0.50 mg/ml) as five different lines in the test area. These antigens were recombinant, synthetic peptides and native antigens. Protein A diluted with PBS 7.4 to a concentration of 0.25 mg/ml was immobilized as a control line. Protein A (Zymed, USA) conjugated with purple colloidal gold particles of approximately 40 nm was sprayed on the conjugate pad and used as the detection system.

Test procedure—The test procedure was the same as Example 1 except that sample volumes of 10 µl of serum were utilized.

Test results—Commercial HIV panel samples (BBI Inc, USA, Zeptometrix Inc, USA and Teragenix Inc USA) were evaluated with this assay. The results showed that DPP HIV confirmatory test detected correctly HIV1 and HIV2 samples and had a 100% correlation with Western Blot and EIA.

Example 4

HIV Test

Test devices substantially identical to the test devices of Example 1 were prepared with the difference that Strip 1 was made longer in each test such that instead of Strip 1 and Strip 2 forming a "T", they formed a "+" configuration. The results were as in Example 1.

Example 5

HIV Test

Test devices substantially as in Example 1 were prepared except that the test and control lines are applied to Strip 1 instead of Strip 2. The results were as in Example 1.

Example 6

HIV Test

Test devices substantially as in Example 1 were prepared except that in the test area a polyclonal antibody against a P24 HIV antigen was immobilized on the test line and a monoclonal antibody against the P24 HIV antigen was conjugated to the colloidal gold. Results showed that a picogram level of P24 antigen could be detected in serum samples.

Example 7

Leptospira Bacteria

Test devices substantially as in Example 1 were prepared except that in the test area, four recombinant lij antigens (A, B, C, D) were mixed and immobilized as the test line. For the conjugate, Protein A/G (Pierce, USA) and anti-human IgM (Sigma, USA) conjugated with purple colloidal gold particles of approximately 40 nm were applied to the conjugate pad. With over 300 endemic samples tested from Brazil and Thailand, an overall sensitivity of approximately 70% with acute phase samples was obtained, and approximately 90% with convalescent phase samples was obtained, and a specificity of approximately 95%.

There have been described and illustrated herein several embodiments of immunoassays and methods of their use. While particular embodiments of the invention have been described, it is not intended that the invention be limited thereto, as it is intended that the invention be as broad in scope as the art will allow and that the specification be read likewise. Thus, while the specification discusses ligand binding using antigen/antibody reactions, other ligand binding mechanisms such as aptamer binding, nucleic acid binding, enzymatic binding, etc. may also be used. Also, while the test cells are described as having a single line for testing for a single ligand, two lines for testing for two ligands, three lines for testing for three ligands, and five test lines for testing five ligands, it will be appreciated that different numbers of lines may be utilized for testing for different numbers of ligands. In such a case, a single housing may be utilized with a single hole for the sample, or alternatively, multiple holes could be utilized if desired. Where multiple holes are utilized, multiple strips may be used for one or more samples provided. Preferably, the multiple strips would touch (e.g., overlie or underlie) a single strip providing a migration path for the conjugate. It may also be possible to provide a single hole which sits over or leads to two adjacent strips adapted for sample migration. Further, while the test cells are described as having holes in the top wall of a housing for receiving the sample and the buffer-solution or buffer-conjugate subsystem, it will be appreciated that one or both holes may be provided in the end wall or side wall of the housing. Similarly, while the sorbent material was described as preferably including a thin plastic backing, it will be appreciated that the plastic backing could be provided only at certain locations or not be provided at all. Where only partial backings or no backings are provided, the test and control sites can be located on either or both sides of the sorbent material. Further yet, while a test strip and control strip are shown is being rectangular in configuration (i.e., lines), it will be appreciated that the test and control sites can be configured differently such as in circles, squares, ovals, a broken line, etc. In fact, the test site and control site can be configured differently from each other. Also, while the invention was described as utilizing a T-shaped housing, and utilizing sorbent materials which are perpendicular to each other, it will be appreciated that the housing could take different shapes (e.g., rectangular, pistol-shaped) while providing sorbent materials which are perpendicular to each other. Further, if desired, the sorbent materials need not be perpendicular to each other, provided distinct migration paths are provided for the analyte/sample and the buffer-conjugate subsystem. Thus, for example, a Y-shaped arrangement can be provided. In fact, it is even possible to provide a rectangular arrangement where, for example, the sample area and sorbent material are located above (or below) the test and control lines and reservoir and separated therefrom by a wall in the housing, and the test and control lines are viewable from a window on the other side of the housing.

Those skilled in the art will also appreciate that the housing may be modified in additional ways to include separate windows for each test line. Also, while the invention was described in conjunction with the use of a buffer solution which is added to the migration path of the conjugate and optionally to the migration path of the sample, it will be appreciated that that one or more buffers may be chosen as desired to be added to the migration paths depending upon the test or tests to be conducted. Thus, buffers such as phosphate buffers or TRIS (tris hydroxymethylaminomethane) buffers are often utilized. However, the invention is intended to encompass the use of any diluent including water. In addition, the diluent may, if needed, may be added to and mixed with the sample prior to adding the sample to the sorbent material or the sample may be deposited first and the diluent may be added thereafter. Likewise, any diluent capable of causing conjugate to migrate may be utilized, and may be premixed with the conjugate in a liquid conjugate system, or provided to the migration path for the conjugate in a dry conjugate system. It will therefore be appreciated by those skilled in the art that yet other modifications could be made to the provided invention without deviating from its spirit and scope as claimed.

What is claimed is:

1. A test device for use with a solution and for use with a conjugate having a marker, the test device for determining the presence of a plurality of different ligands in a liquid sample, the test device comprising:
   a) a first sorbent strip having a first location for receiving a solution and defining a first migration path for the solution and the conjugate;
   b) a second sorbent strip distinct from said first sorbent strip having a second location for receiving the liquid sample and defining a second migration path for the sample distinct from said first migration path; and
   c) a test site located on or in said first sorbent strip and/or said second sorbent strip, said test site having a plurality of separate immobilized ligand-binding mechanisms for separately binding to respective of the plurality of different ligands, and said first and second sorbent strips touching each other at the test site, and said second migration path extending laterally from said second location to at least said test site such that application of the liquid sample to the second location requires time for the liquid sample to laterally flow to the test site and does not immediately wet the test site upon application.

2. A test device according to claim 1, wherein:
said plurality of separate immobilized ligand-binding mechanisms are arranged in at least four lines containing respectively different HIV antigens or antibodies.

3. A test device according to claim 2, wherein:
said different HIV antigens or antibodies comprise at least four of p24, gp41, gp120, gp160 and gp36.

4. A test device according to claim 1, further comprising:
said conjugate, wherein
said first sorbent strip supports said conjugate.

5. A test device according to claim 4, wherein:
each said immobilized ligand-binding mechanism is an antigen or antibody for respective of said different ligands, and said conjugate comprises antigens and/or antibodies for the different ligands and a marker coupled to the antigens and/or antibodies.

6. A test device according to claim 5, wherein:
said marker is a colored marker viewable in the visible spectrum.

7. A test device according to claim 1, wherein:
said first sorbent strip and said second sorbent strip are arranged in a "T" configuration or a "+" configuration.

8. A test device according to claim 1, wherein:
said first sorbent strip has a first pore size and said second sorbent strip has a second pore size.

9. A test device according to claim 1, wherein:
at least a portion of said test site is dyed with a visible colored dye.

* * * * *